United States Patent
Amano et al.

(10) Patent No.: US 12,204,176 B2
(45) Date of Patent: Jan. 21, 2025

(54) MOUNTING TOOL

(71) Applicant: SONY CORPORATION, Tokyo (JP)

(72) Inventors: Toru Amano, Tokyo (JP); Yasutaka Fukumoto, Tokyo (JP); Naofumi Fukasawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 18/608,951

(22) Filed: Mar. 19, 2024

(65) Prior Publication Data

US 2024/0219748 A1 Jul. 4, 2024

Related U.S. Application Data

(63) Continuation of application No. 17/255,116, filed as application No. PCT/JP2019/028421 on Jul. 19, 2019, now Pat. No. 11,966,101, which is a continuation-in-part of application No. PCT/JP2019/026790, filed on Jul. 5, 2019.

(30) Foreign Application Priority Data

Jul. 20, 2018 (JP) .................................. 2018-136972

(51) Int. Cl.
*G02C 3/00* (2006.01)
*G06F 3/01* (2006.01)

(52) U.S. Cl.
CPC ............. *G02C 3/003* (2013.01); *G06F 3/012* (2013.01)

(58) Field of Classification Search
CPC ........ G02C 3/003; G02C 5/143; G02C 11/10; G06F 3/012; G06F 3/017; A61B 5/6819; A61B 5/1114; A61B 5/6803
See application file for complete search history.

(56) References Cited

U.S. PATENT DOCUMENTS

| 2006/0119789 A1 | 6/2006 | Bruck |
| 2016/0007921 A1 | 1/2016 | Galea et al. |

(Continued)

FOREIGN PATENT DOCUMENTS

| EP | 1669793 A1 | 6/2006 |
| JP | 2000-325313 A | 11/2000 |

(Continued)

*Primary Examiner* — James C. Jones
(74) *Attorney, Agent, or Firm* — Paratus Law Group, PLLC

(57) ABSTRACT

The present disclosure relates to a mounting tool that makes it possible to sense the position or the orientation of the head in a natural state without impairing the wearing feeling or the appearance. The nose pad of the glasses comes into contact with and fixes the nose, which is the frontal region of the user, an ear hook including an insertion portion that allows the temple of the glasses to be inserted and fixed comes into contact with and fixes an ear, the occipital region fixing unit configured integrally with the ear hook comes into contact with and fixes the occipital region while holding the sensor device that detects the position and the orientation of the head of the user, the occipital region upper portion fixing unit comes into contact with and fixes the occipital region, an insertion portion that allows the temple of the glasses to be inserted is provided, and the occipital region upper portion is fixed. The present disclosure can be applied to motion capture.

11 Claims, 26 Drawing Sheets

(56) References Cited

U.S. PATENT DOCUMENTS

| | | | |
|---|---|---|---|
| 2017/0307903 A1 | 10/2017 | Calilung et al. | |
| 2018/0082656 A1 | 3/2018 | Ito et al. | |
| 2018/0348863 A1* | 12/2018 | Aimone | ................ G06F 3/147 |

FOREIGN PATENT DOCUMENTS

| | | |
|---|---|---|
| JP | 2006-163386 A | 6/2006 |
| JP | 2009-506442 A | 2/2009 |
| JP | 5362357 B2 | 12/2013 |
| JP | 2016-126500 A | 7/2016 |
| JP | 2016-197198 A | 11/2016 |
| JP | 2017-092628 A | 5/2017 |
| WO | WO 2016/170854 A1 | 10/2016 |
| WO | WO 2017/010276 A1 | 1/2017 |

* cited by examiner

FIG. 9
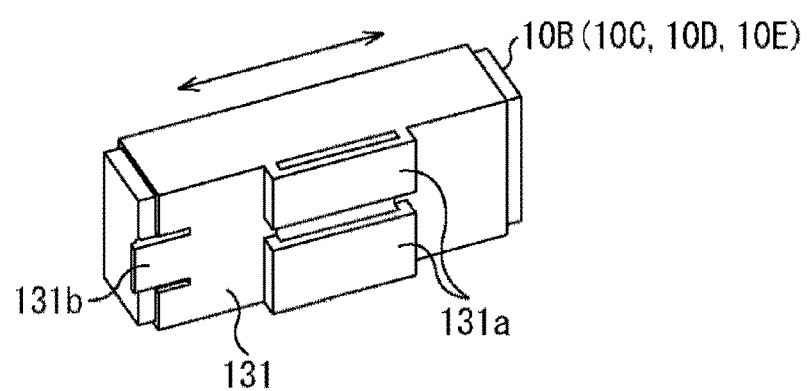
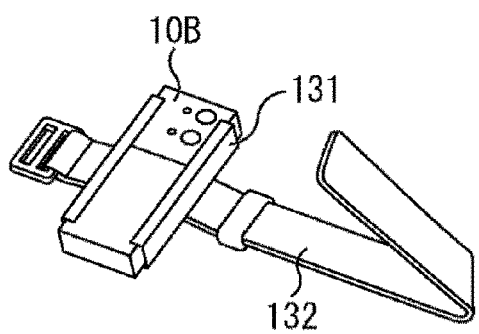
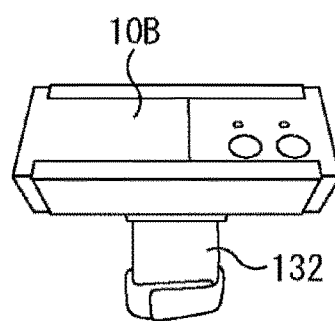

FIG. 10
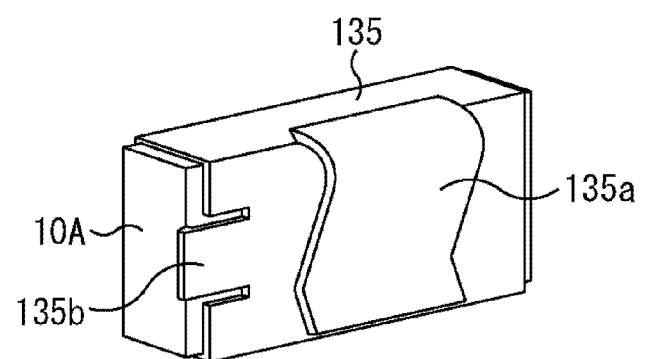
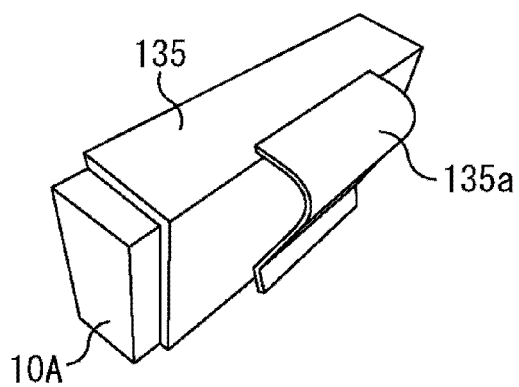

MOUNTING TOOL

CROSS REFERENCE TO PRIOR APPLICATION

This application is a continuation of U.S. patent application Ser. No. 17/255,116 (filed on Dec. 22, 2020), which is a National Stage Patent Application of PCT International Patent Application No. PCT/JP2019/028421 (filed on Jul. 19, 2019) under 35 U.S.C. § 371, which is a continuation-in-part of PCT International Patent Application No. PCT/JP2019/026790 (filed on Jul. 5, 2019), which claims priority to Japanese Patent Application No. 2018-136972 (filed on Jul. 20, 2018), which are all hereby incorporated by reference in their entirety.

TECHNICAL FIELD

The present disclosure relates to a mounting tool, and more particularly to a mounting tool capable of sensing the position or the orientation of the head in a natural state without impairing the wearing feeling or the appearance.

BACKGROUND ART

A technology for sensing the state (facial expression) of the head has been proposed (see Patent Document 1) as a technology to be applied to motion capture.

CITATION LIST

Patent Document

Patent Document 1: Japanese Patent Application National Publication (Laid-Open) No. 2009-506442

SUMMARY OF THE INVENTION

Problems to be Solved by the Invention

However, in the technology described in Patent Document 1, it is necessary to mount a helmet-shaped wearable device that wraps the entire head, and the wearable device is large-scale.

Accordingly, when trying to sense the position or the orientation of the head in normal life using the wearable device of Patent Technology 1, it is impossible to prompt the wearer to natural operation, and therefore it may possibly be impossible to sense the position or the orientation of the head appropriately.

Furthermore, since a helmet-shaped wearable device must be worn, the appearance becomes strange and cannot be said to be stylish.

The present disclosure has been made in view of such a situation and, in particular, is designed to enable sensing of the position or the orientation of the head in a natural state without impairing the wearing feeling or the appearance.

Solutions to Problems

A mounting tool of one aspect of the present disclosure is a mounting tool including: a frontal region fixing unit that comes into contact with and fixes the frontal region of the user; an occipital region fixing unit that comes into contact with and fixes the occipital region of the user; and a sensor device fixing unit configured to fix a sensor device that is provided on a rear surface of the occipital region fixing unit with respect to a surface to come into contact with the occipital region of the user and detects the position and the orientation of the head of the user.

In one aspect of the present disclosure, the frontal region fixing unit comes into contact with and fixes the frontal region of the user, the occipital region fixing unit comes into contact with and fixes the occipital region of the user, and the sensor device fixing unit fixes the sensor device that is provided on the rear surface of the occipital region fixing unit with respect to a surface to come into contact with the occipital region of the user and detects the position and orientation of the head of the user.

Effects of the Invention

It becomes possible with one aspect of the present disclosure to sense the position or the orientation of the head in a natural state without impairing the wearing feeling or the appearance.

BRIEF DESCRIPTION OF DRAWINGS

FIG. 9 is a view illustrating an example of mounting a sensor device on the wrists and the ankles.

FIG. 10 is a view illustrating an example of mounting a sensor device on the waist part.

MODE FOR CARRYING OUT THE INVENTION

Figure 1:
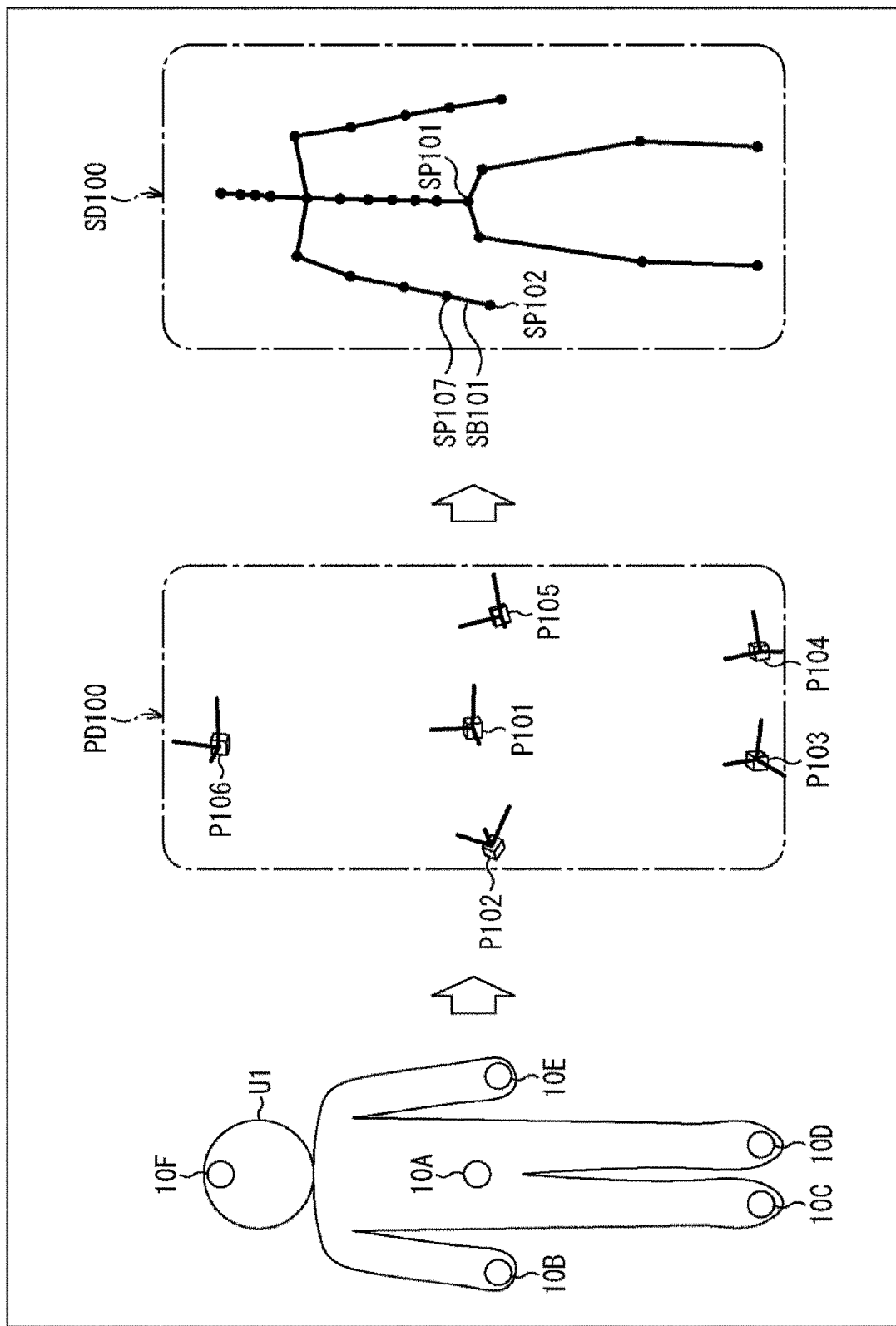
FIG. 1 is a diagram illustrating an outline of motion capture of the present disclosure.

The following description will explain preferred embodiments of the present disclosure in detail with reference to the accompanying drawings. In the present specification and the drawings, note that components having substantially the same functional configurations are designated by the same reference numerals to omit duplicate description.

The following description will explain modes for carrying out the present technology. The description will be given in the following order.

1. Outline of motion capture
2. Configuration example of motion capture system of present disclosure
3. Configuration example of sensor device
4. Example of mounting sensor device on wrists, ankles, and waist part
5. Example of mounting sensor device on head
6. Configuration example of insertion portion
7. Modified example of occipital region upper portion fixing unit
8. Modified example of configuration that comes into contact with frontal region
9. First application example
10. Second application example
11. Third application example
12. Fourth application example
13. Fifth application example 1. Outline of Motion Capture In description of a mounting device (mounting tool) for mounting a sensor device of the present disclosure on the head, an outline of a motion capture system to which the mounting device of the present disclosure is applied will be described first.

In order to visualize information on movement of the body of a human, an animal, or the like, skeleton information represented by a skeleton structure indicating the structure of the body is used, for example. The skeleton structure contains information on sites, and bones that are line segments connecting the sites. Note that a site in the skeleton structure corresponds to, for example, a terminal site or a joint site of the body, or the like. Furthermore, although bones in a skeleton structure can correspond to human bones, for example, the positions or the number of bones do not necessarily have to be consistent with actual human skeleton.

The position of a site in skeleton information can be acquired by mounting a marker, or mounting a motion sensor, on each corresponding site of the body, for example. For example, there is a technology of mounting a marker on each site of the body so as to acquire the position of the marker using an external camera or the like, or a technology of mounting a motion sensor on a site of the body so as to acquire the position information of the motion sensor on the basis of sensor data acquired by the motion sensor.

In comparison with the technology that uses a marker mounted on the body, the technology that uses a motion sensor mounted on the body has an advantage that an external camera, a light source, and a marker are unnecessary, and it is portable and easy to set up. Furthermore, the technology that uses a motion sensor mounted on the body is not limited by the image capturing range of the camera and therefore has an advantage that it can be used in a wide outdoor space, a space with a complicated shape where blind spots are likely to occur, a narrow space, or the like.

However, in order to estimate the skeleton of the whole body in the technology that uses a motion sensor mounted on the body, it is necessary to mount the motion sensor on each joint, which may impose a heavy load on the user. Furthermore, although an exclusive suite for appropriately mounting a large number of motion sensors on respective sites of the user has been developed, the exclusive suite may require a high manufacturing cost.

Therefore, a motion capture system has been proposed that acquires position information of more sites than the mounted motion sensors while reducing the number of mounted motion sensors. In the present disclosure, note that a motion sensor is a device that senses movement of the body, and may include an inertial sensor (acceleration sensor, angular velocity sensor), a geomagnetic sensor, an atmospheric pressure sensor, an image sensor, or the like. The following description will mainly explain an example in which at least an inertial sensor is mounted on the body as a motion sensor.

FIG. 1 is a diagram illustrating an outline of a motion capture system. In the example illustrated in FIG. 1, six sensor devices 10A to 10F are mounted on six sites of the body of a user U1. The sensor devices 10A to 10F include, for example, an inertial sensor (IMU: Inertial Measurement Unit) such as an acceleration sensor that acquires acceleration or a gyro sensor (angular velocity sensor) that acquires angular velocity.

It is desirable that the sensor devices 10A to 10F be mounted on a joint site that serves as a reference for the body (e.g., waist or head) or in the vicinity of an end of the body (such as wrist, ankle, head, or the like). In the example illustrated in FIG. 1, the sensor device 10A is mounted on the waist of the user U1, the sensor devices 10B and 10E are mounted on the wrists, the sensor devices 10C and 10D are mounted on the ankles, and the sensor device 10F is mounted on the head.

In the following description, note that the sensor devices 10A to 10F may be collectively referred to as a sensor device 10 in a case where it is unnecessary to distinguish the sensor devices. Furthermore, in the following description, a site of the body on which a sensor device 10 is mounted may also be referred to as a mounting site. Furthermore, the number of sensor devices 10 or the mounting positions (positions of mounting sites) is not limited to the example illustrated in FIG. 1.

The motion capture system of FIG. 1 acquires information on the position and the orientation of each mounting site on the basis of sensor data acquired by the sensor device 10. FIG. 1 illustrates mounting site information PD100 including position information and orientation information as information regarding mounting sites P101 to P106 on which the sensor devices 10A to 10F are mounted (which will be hereinafter also referred to as mounting site information).

Furthermore, the motion capture system of FIG. 1 estimates skeleton information including position information and orientation information of each site in the skeleton structure on the basis of the position information and the orientation information of the mounting sites P101 to P106 on which the sensor devices 10A to 10F are mounted. Here, in the present embodiment, position information and orientation information of not only a mounting site where a sensor device 10 is mounted among sites in the skeleton structure but also a site (which will be hereinafter also referred to as a non-mounting site) where a sensor device 10 is not mounted is estimated.

In the example of FIG. 1, skeleton information SD100 including the position information and the orientation information of each site in the skeleton structure is illustrated. The skeleton information SD100 includes not only information on mounting site SP101 corresponding to the mounting site P101 or information on mounting site SP102 corresponding to the mounting site P102 but also information on non-mounting site SP107.

Note that the skeleton information can include bone information (position information, orientation information, and the like) in addition to site information. For example, in the example illustrated in FIG. 1, the skeleton information SD100 can include information on bone SB101. For example, it is possible to specify bone information between sites on the basis of the position information and the orientation information of sites in the skeleton structure.

As described above, it is possible with the present embodiment to reduce the number of motion sensors to be mounted while maintaining the number of sites for which information is desired to be acquired, by estimating information on a non-mounting site where a motion sensor is not mounted on the basis of information on a mounting site where a motion sensor is mounted.

That is, there is a technology of acquiring skeleton information by forward kinematics (FK) calculation as an existing motion capture technology. Forward kinematics calculation is a method of calculating the position of an end site on the basis of the orientation of each joint site.

However, in order to specify the position information on each site using the forward kinematics calculation, the orientation information on each joint site is necessary, and using the forward kinematics calculation causes an increase in the number of motion sensors to be mounted on the body.

Therefore, it is conceivable to acquire skeleton information by using inverse kinematics (IK) calculation instead of the forward kinematics calculation described above. Inverse kinematics calculation is a method of calculating the orientation of each joint site on the basis of the position of a terminal region.

That is, since the orientation of each joint site is calculated only by the sensor devices 10A to 10F provided at terminal regions by using inverse kinematics calculation, the user only needs to mount the minimum necessary motion sensors. Therefore, more natural movement can be realized even when the motion sensors are mounted, and as a result, motion capture corresponding to more natural movement can be realized.

2. Configuration Example of Motion Capture System of Present Disclosure

Figure 2:
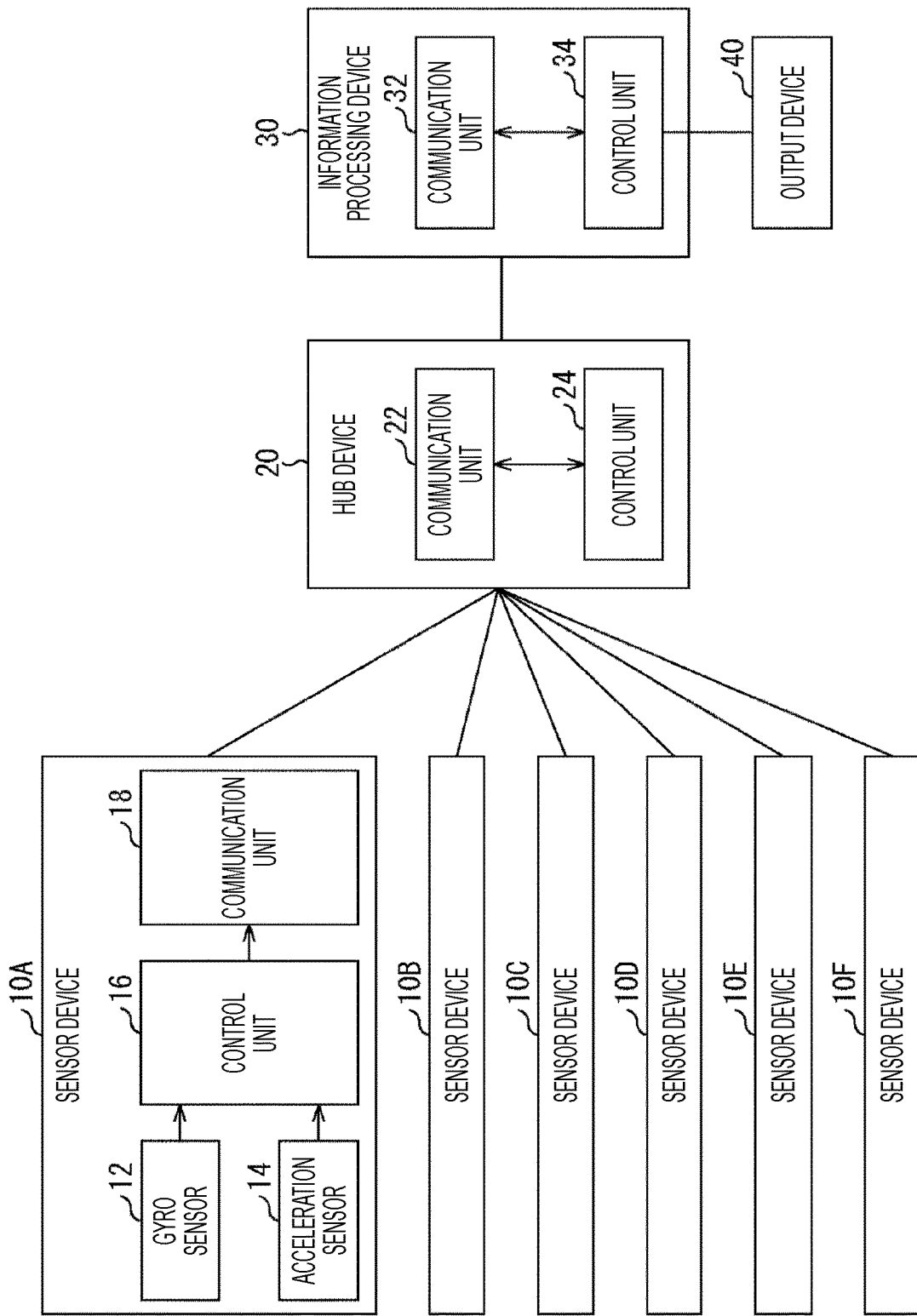
FIG. 2 is a diagram illustrating a configuration example of a motion capture system of the present disclosure.

Next, a configuration example of a motion capture system of the present disclosure will be described with reference to FIG. 2. As illustrated in FIG. 2, the motion capture system of the present disclosure includes the sensor devices 10A to 10F, a hub device 20, an information processing device 30, and an output device 40.

The sensor device 10 includes at least a motion sensor and is a device to be mounted on a body site. Since sites on which the sensor devices 10A to 10F are mounted have been described with reference to FIG. 1, the description thereof is omitted here.

The sensor device 10 includes a gyro sensor 12, an acceleration sensor 14, a control unit 16, and a communication unit 18, for example, as illustrated in FIG. 2. Note that the motion sensor included in the sensor device 10 is not limited to an inertial sensor (gyro sensor 12 and acceleration sensor 14). For example, the sensor device 10 may include a motion sensor such as a geomagnetic sensor, an atmospheric pressure sensor, or an image sensor instead of the inertial sensor or in addition to the inertial sensor. Furthermore, although only the configuration of the sensor device 10A is illustrated in FIG. 2, the configurations of the sensor devices 10A to 10F may be the same.

The gyro sensor 12 is an inertial sensor that acquires an angular velocity as sensor data. The angular velocity acquired by the gyro sensor 12 can be the angular velocity of the sensor device 10 in the local coordinate system.

Furthermore, the acceleration sensor 14 is an inertial sensor that acquires acceleration as sensor data. The acceleration acquired by the acceleration sensor 14 can be the acceleration of the sensor device 10 in the local coordinate system set for each sensor device 10.

The control unit 16 controls the operation of the sensor device 10. For example, the control unit 16 may control communication by the communication unit 18 and transmit the sensor data (angular velocity and acceleration) acquired by the gyro sensor 12 and the acceleration sensor 14 to the hub device 20. Alternatively, the control unit 16 may perform processing on the sensor data acquired by the gyro sensor 12 and the acceleration sensor 14, and may transmit the processing result obtained by this processing to the hub device 20.

The communication unit 18 is a communication module for transmitting and receiving data to and from other devices by wire or wirelessly. The communication unit 18 wirelessly communicates with an external equipment directly or via a network access point using a method such as a wired local area network (LAN), a wireless LAN, Wi-Fi (Wireless Fidelity, registered trademark), infrared communication, Bluetooth (registered trademark), or short-range/contactless communication, for example.

The hub device 20 is an information processing device that receives and aggregates information from a plurality of sensor devices 10. Note that the sensor device 10 and the hub device 20 may be connected by wire or wirelessly. The hub device 20 includes, for example, a communication unit 22 and a control unit 24 as illustrated in FIG. 2.

The communication unit 22 is a communication module for transmitting and receiving data to and from other devices by wire or wirelessly. The communication unit 22 wirelessly communicates with an external equipment directly or via a network access point using a method such as a wired LAN, a wireless LAN, Wi-Fi, infrared communication, Bluetooth, or short-range/contactless communication, for example.

The control unit 24 controls the operation of the hub device 20. For example, the control unit 24 may control communication by the communication unit 22 and transmit the information received from the sensor device 10 to the information processing device 30 immediately. Alternatively, the control unit 24 may perform processing on the information received from the sensor device 10, and transmit the processing result obtained by this processing to the information processing device 30.

The information processing device 30 is an information processing device that receives and processes information from the hub device 20. Note that the hub device 20 and the information processing device 30 may be connected by wire or wirelessly. The information processing device 30 includes, for example, a communication unit 32 and a control unit 34 as illustrated in FIG. 2.

The communication unit 32 is a communication module for transmitting and receiving data to and from other devices by wire or wirelessly. The communication unit 32 wirelessly communicates with an external equipment directly or via a network access point using a method such as a wired LAN, a wireless LAN, Wi-Fi, infrared communication, Bluetooth, or short-range/contactless communication, for example.

The control unit 34 controls the operation of the information processing device 30. For example, the control unit 34 processes the information received by the communication unit 32. Furthermore, the control unit 34 can control the display of the output device 40 by causing the communication unit 32 to transmit the result of this processing to the output device 40 connected to the information processing device 30. For example, the control unit 34 may display the visualized skeleton information, the 3D model reflecting the skeleton information, or the like on the output device 40 on the basis of the skeleton information obtained as a result of the processing.

The output device 40 is a device having at least a display function, and performs display according to the control of the control unit 34 of the information processing device 30. The output device 40 may be, for example, a stationary display or a head mounted display (HMD) to be worn by the user. Furthermore, the output device 40 and the information processing device 30 may be an integrated device.

3. Configuration Example of Sensor Device

Figure 3:
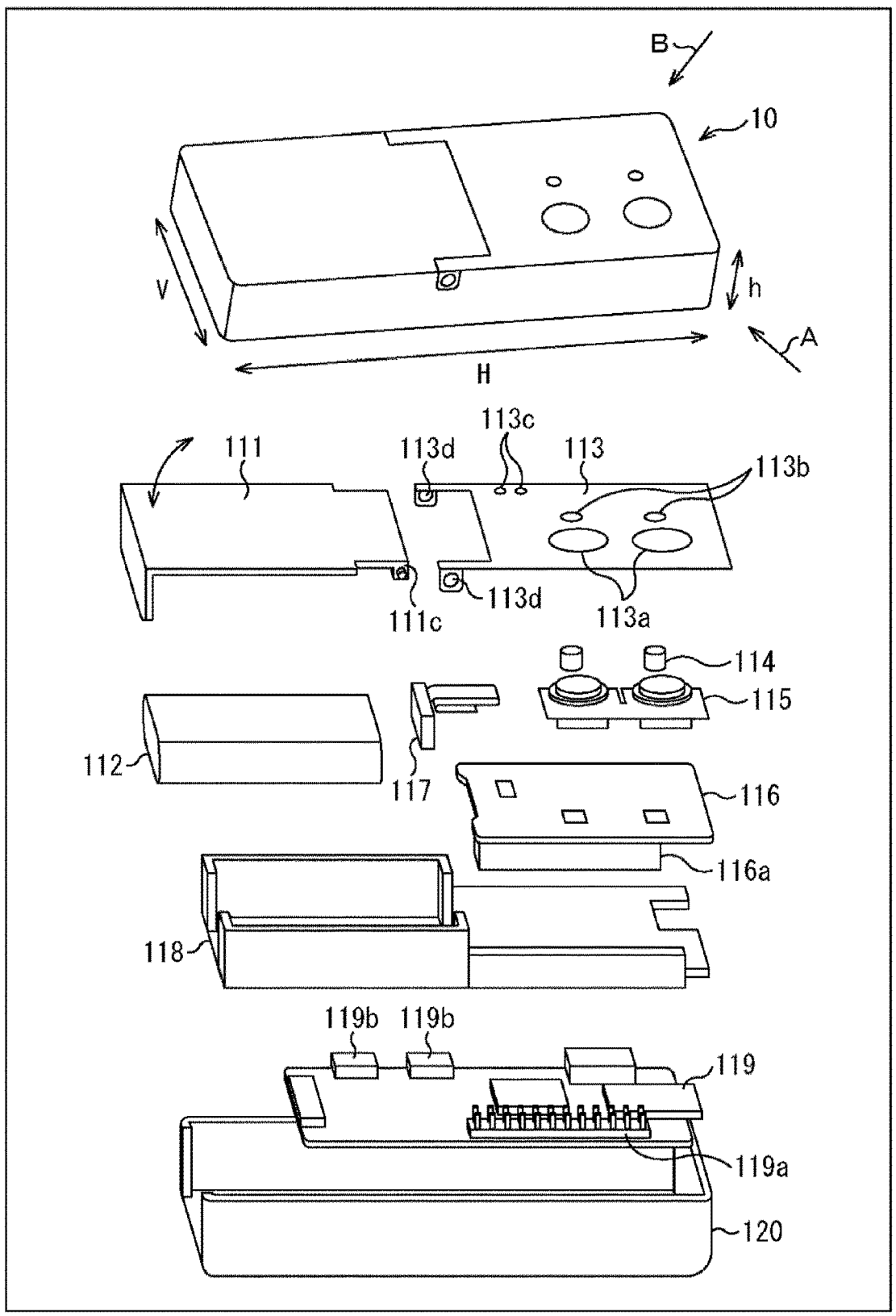
FIG. 3 is an exploded view of a sensor device of the present disclosure.
Figure 4:
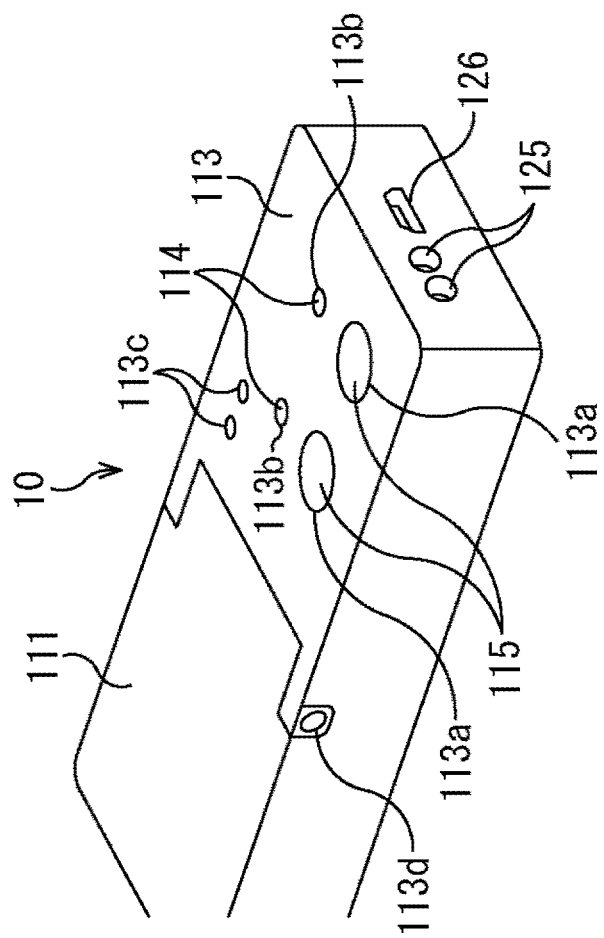
FIG. 4 is a perspective view of a sensor device of the present disclosure.
Figure 5:
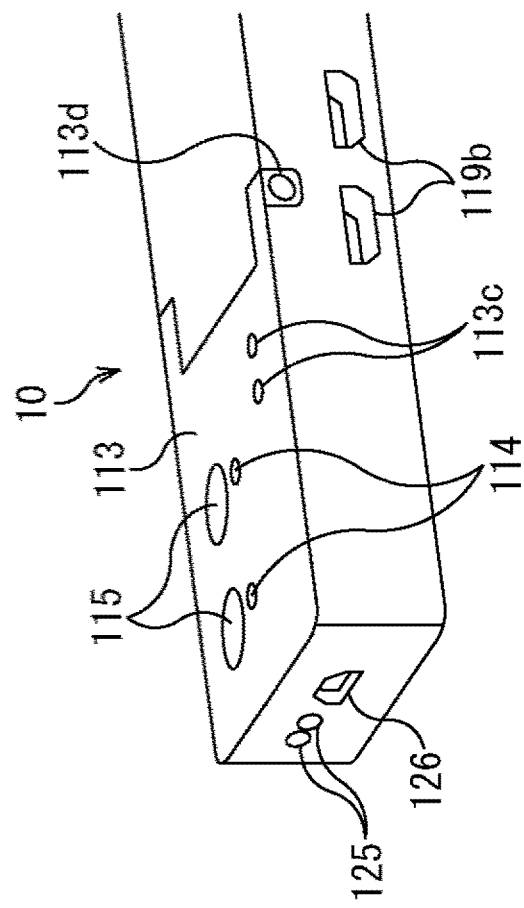
FIG. 5 is a perspective view of a sensor device of the present disclosure.
Figure 6:
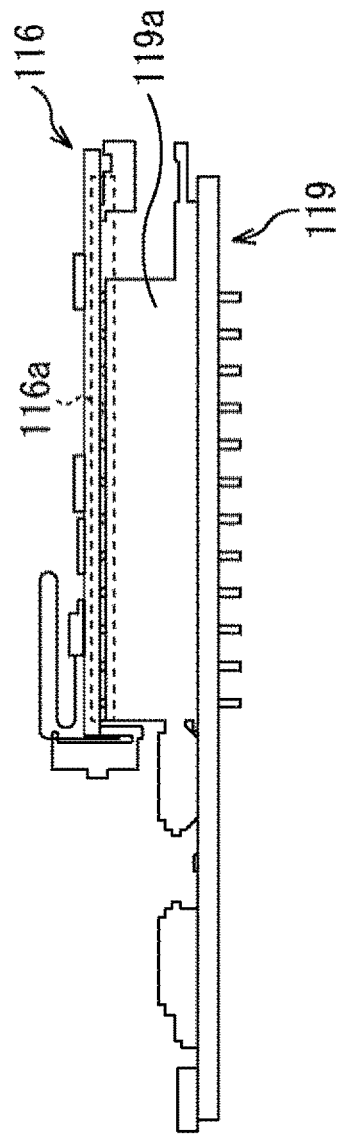
FIG. 6 is a view illustrating a configuration example of a sensor board of the present disclosure.
Figure 7:
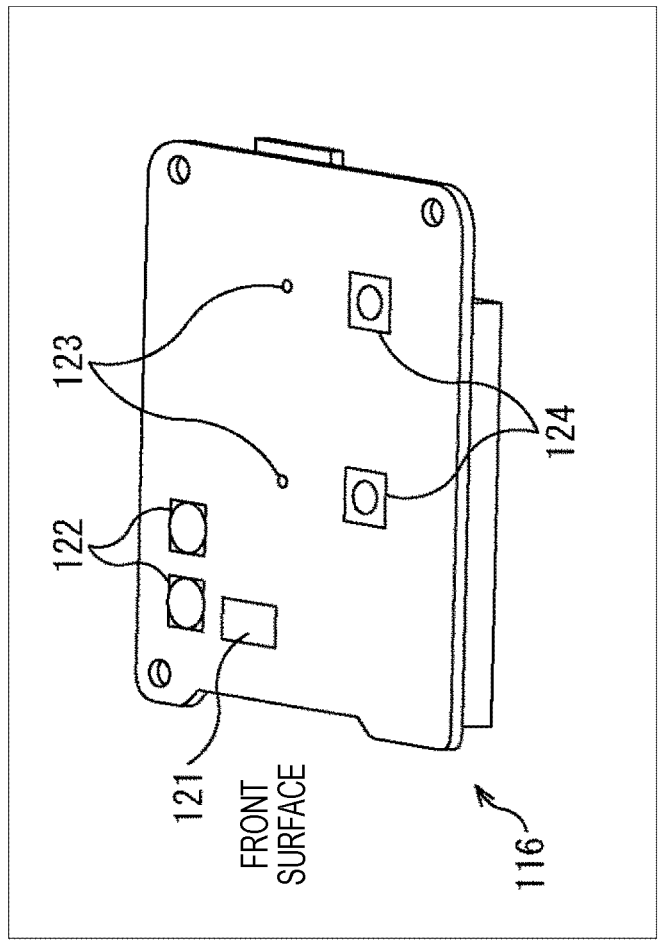
FIG. 7 is a view illustrating a configuration example of a sensor board of the present disclosure.
Figure 8:
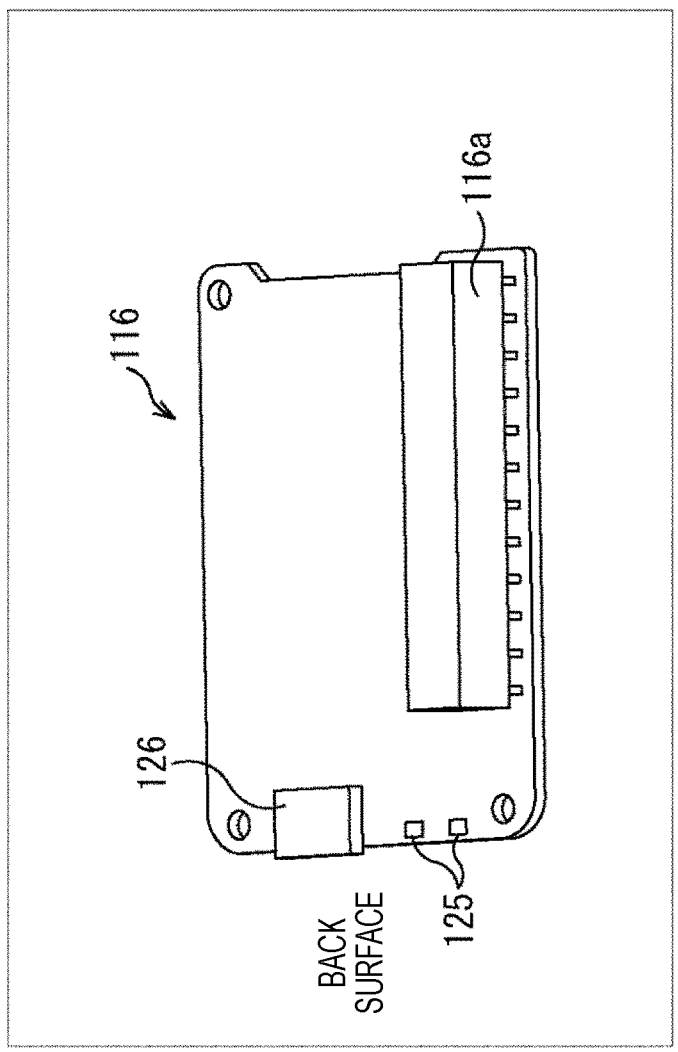
FIG. 8 is a view illustrating a configuration example of a sensor board of the present disclosure.

Next, a configuration example of the sensor device 10 will be described with reference to FIGS. 3 to 8. Note that FIG. 3 is an exploded view of the sensor device 10, and FIG. 4 is a perspective view of the sensor device 10 in the uppermost section of FIG. 3 viewed in the direction of arrow A. Furthermore, FIG. 5 is a perspective view of the sensor device 10 in the uppermost section of FIG. 3 viewed in the direction of arrow B, and FIG. 6 is a side view of a sensor board 116 and a computer board 119 in FIG. 3 in a connected state. Moreover, FIG. 7 is a front view of the sensor board 116, and FIG. 8 is a back view of the sensor board 116.

In description of the arrangement of the sensor device 10, note that the explanation will proceed with reference to the uppermost section of FIG. 3.

As illustrated in the uppermost section of FIG. 3, the sensor device 10 is a rectangular structure having a width H in the horizontal direction, a width V in a perpendicular direction, and a height h.

Here, H of the sensor device 10 is, for example, 86.6 mm, V is, for example, 34.8 mm, and h is, for example, 16.1 mm. Note that this size is an example and the present invention is not limited to this size.

Furthermore, as illustrated in FIG. 3, the sensor device 10 includes a battery lid 111, a battery 112, a front case 113, light guide tubes 114, buttons 115, the sensor board 116, a battery connector 117, an inner case 118, the computer board 119, and a back case 120.

The battery lid 111 is configured to be opened and closed with respect to the sensor device 10 in the arrow direction about a shaft 111a by fitting a shaft 111c with holes 113d of the front case 113, and the battery 112 can be made detachable with respect to the battery connector 117 provided at the inner case 118 when the battery lid 111 is opened. Furthermore, the battery 112 can be stored in the inner case 118 when the battery lid 111 is closed.

The sensor board 116 is configured to function as the gyro sensor 12 or the acceleration sensor 14 in FIG. 2, and a relay terminal 116a is physically and electrically connected with a relay terminal 119a of the computer board 119 as illustrated in FIG. 6. Then, the sensor board 116 operates on the basis of a control signal supplied from the computer board 119 via the relay terminals 116a and 119a, and outputs the sensing result to the computer board 119.

Furthermore, a connector 121, switches 122, LEDs 123, and switches 124 are provided on the surface of the sensor board 116 as illustrated in FIG. 7.

The connector 121 is connected with the battery connector 117 and receives power supplied from the battery 112.

The switches 122 are provided at positions corresponding to holes 113c provided at the front case 113 (FIG. 3), and directly accept a pressing operation via the holes 113c.

The LEDs 123 emit light according to the operation state of the sensor board 116 so as to cause the user visually recognize the operation state. The light guide tubes 114 provided at the front case 113 (FIG. 3) are in contact with upper portions of LEDs 123, and light from the LEDs 123 is guided to the holes 113b of the front case 113 via the light guide tubes 114 and emitted.

The switches 124 are provided at positions corresponding to the buttons 115 provided in a state of being exposed from the holes 113a of the front case 113 (FIG. 3), and accept a pressing operation via the buttons 115.

Moreover, LEDs 125, a p USB terminal 126, and a relay terminal 116a are provided on the back surface of the sensor board 116 as illustrated in FIG. 8.

The LEDs 125 emit light according to the operation state of the sensor board 116 so that the operation state can be visually recognized by the user, and are provided at positions corresponding to the right side surface of the sensor device 10 in the uppermost section of FIG. 3 as illustrated in FIG. 4.

As illustrated in FIG. 4, the p USB terminal 126 is provided at a position corresponding to the right side surface of the sensor device 10 at the uppermost section of FIG. 3, and is used for connection with an external device and for external output of sensing results or the like.

The relay terminal 116a is connected with the relay terminal 119a of the computer board 119, physically and electrically connects the computer board 119 and the sensor board 116, and enables transmission and reception of various control signals and data.

Moreover, the computer board 119 is provided with p USB terminals 119b (FIG. 3), which are provided on the side surface in the back direction when viewed from the sensor device 10 in the uppermost section of FIG. 3 as illustrated in FIG. 5, and are used for connection with an external device and for external output of sensing results or the like.

The computer board 119 has a configuration corresponding to the control unit 16 and the communication unit 18 in FIG. 2, and executes processing such as processing various sensing results, storing various sensing results, and outputting various sensing results to the information processing device 30 via the hub device 20.

4. Example of Mounting Sensor Device on Wrists, Ankles, and Waist Part

Next, an example of mounting the sensor device 10 on the wrists, the ankles, and the waist part will be described.

In a case where the sensor devices 10B to 10E are mounted on the wrists and ankles, for example, the mounting tool 131 illustrated in the upper section of FIG. 9 is used.

The mounting tool 131 is a concave bracket and, as illustrated in the upper section of FIG. 9, exposes a surface part of the sensor device 10 in the uppermost section of FIG. 3 in a state of sandwiching side surfaces (side surfaces on the near side and far side, and the rear surface in the sensor device 10 in the uppermost section of FIG. 3) of the sensor device 10B (or any one of 10C to 10E), so as to allow the surface part to be inserted into the mounting tool 131 in the arrow direction in the figure, and fix the surface part by a claw portion 131b.

Furthermore, the mounting tool 131 is provided with belt holes 131a as illustrated in the upper section of FIG. 9, and a belt 132 is passed through the belt holes 131a as illustrated in the middle section and the lower left section of FIG. 9. Then, by winding this belt 132 around the wrist or the ankle, the sensor device 10B (or any one of 10C to 10E) is fixed to and mounted on the wrist or the ankle.

Regarding the belt 132, note that a non-stretchable material may be used in a case where the belt is used for the wrist, and a stretchable material may be used in a case where the belt is used for the ankle.

Furthermore, in a case where the sensor device 10A is mounted on the waist part, for example, a mounting tool 135 illustrated in the upper and lower sections of FIG. 10 is used.

The mounting tool 135 is also constituted of a concave bracket, and the sensor device 10A is fixed by a claw portion 135b in a manner similar to the mounting tool 135.

A clip 135a is provided on the mounting tool 135, and the sensor device 10A is fixed to and mounted on the waist part by hanging the clip on a belt part worn by the user U1 or on a waist part of trousers.

5. Example of Mounting Sensor Device on Head

Figure 11:
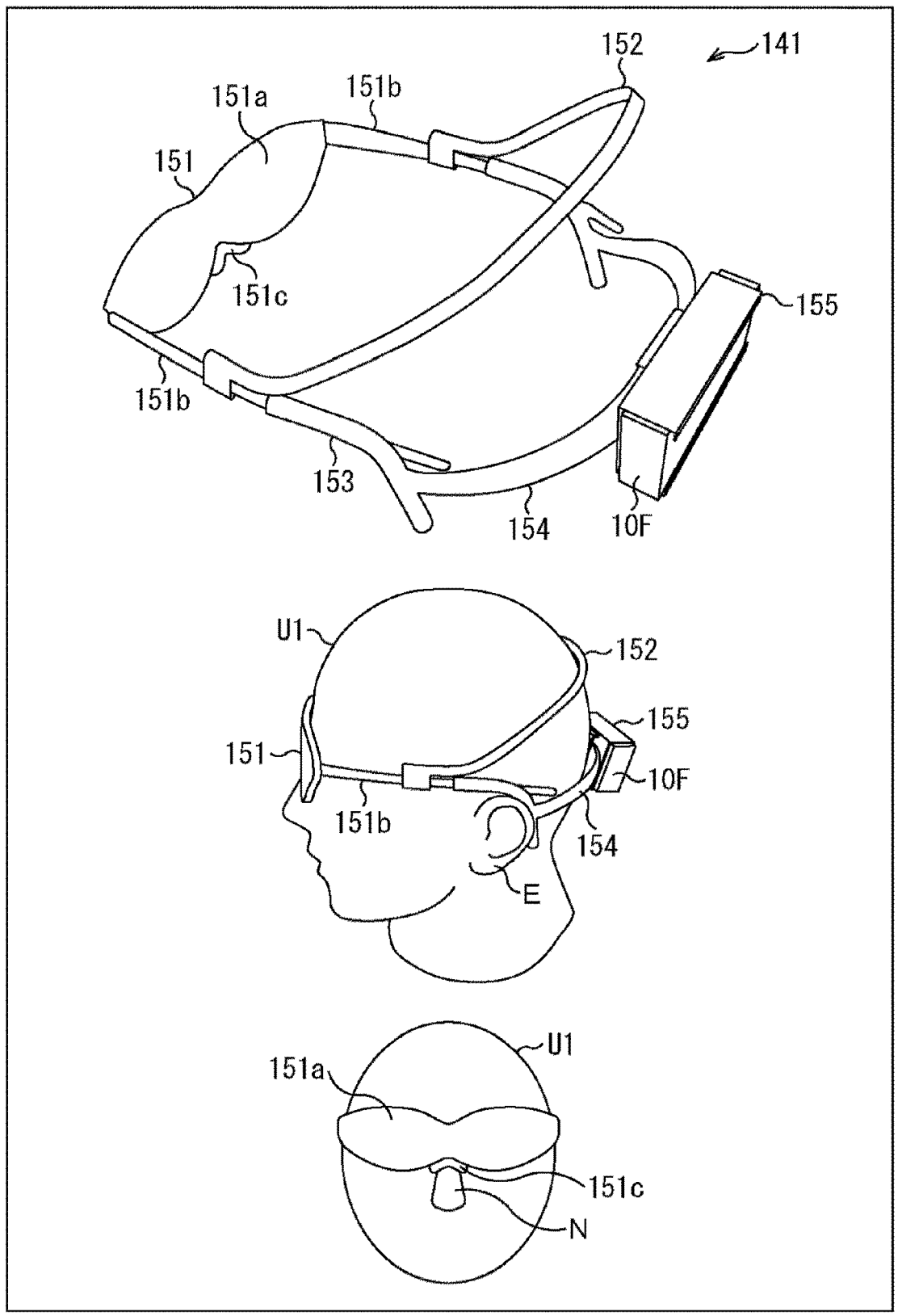
FIG. 11 is a view illustrating an example of mounting a sensor device on the head.
Figure 12:
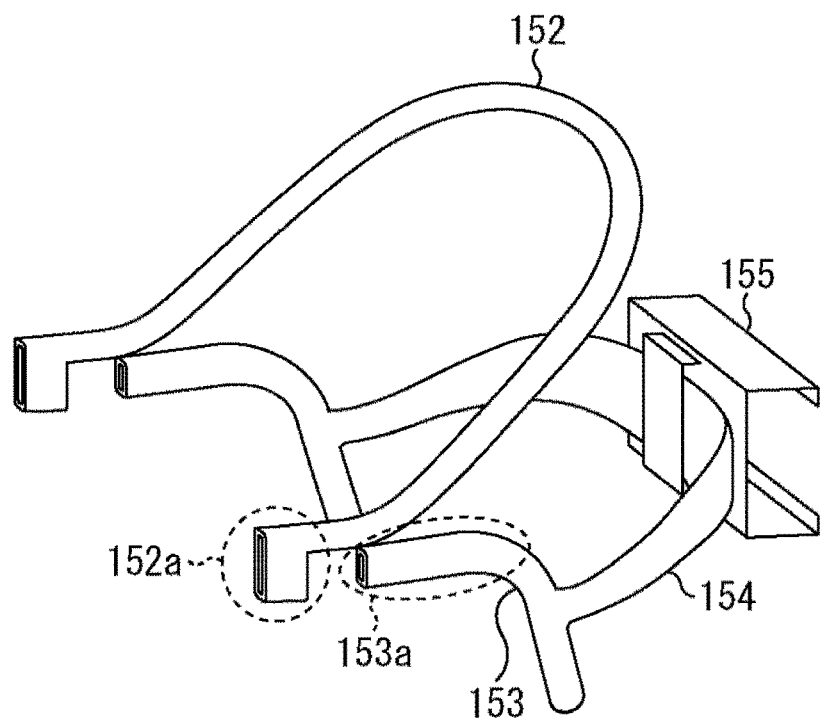
FIG. 12 is a view illustrating an example of mounting a sensor device on the head.

Next, a configuration example of a mounting tool 141 of a case where the sensor device 10F is mounted on the head will be described with reference to FIGS. 11 and 12. In FIG. 11, note that the upper section is an external perspective view of the mounting tool 141, the middle section is a side view of the user U1 of a case where the sensor device 10F is mounted on the head of the user U1 using the mounting tool 141, and the lower section is a view of the user U1 of a case where the sensor device 10F is mounted using the mounting tool 141 viewed from the front. Furthermore, FIG. 12 is an external perspective view of the state in which glasses 151, which is a part of the mounting tool 141, are detached.

As illustrated in the upper section of FIG. 11, the mounting tool 141 includes the glasses 151, an occipital region upper portion fixing unit 152, ear hooks 153, an occipital region fixing unit 154, and a bracket portion 155.

The glasses 151 are general glasses or sunglasses in which a frame 151a functions as ordinary glasses or sunglasses covering the eyes of the user U1. Furthermore, temples (bows) 151b of the glasses 151 are inserted into insertion portions 152a provided at tip portions of the occipital region upper portion fixing unit 152 illustrated in FIG. 12, and are inserted into insertion portions 153a provided at tip portions of the ear hooks 153.

Moreover, as illustrated in the middle section of FIG. 11, the ear hooks 153 each have a structure that comes into contact with an upper portion of an ear E of the user U1 and each have a structure integrated with the occipital region fixing unit 154, and the bracket portion 155 for mounting the sensor device 10F is provided at the occipital region fixing unit 154. Note that the bracket 155 may have a configuration fixedly attached to the occipital region fixing unit 154, or may have a detachable configuration. Furthermore, as long as the sensor device 10F can be fixed to the occipital region fixing unit 154, a configuration other than the bracket 155 may be employed, or a configuration in which a bag-shaped device capable of storing the sensor device 10F is provided on the back side of a site of the occipital region fixing unit 154 that comes into contact with the occipital region may be used, for example.

The glasses 151 are provided with a nose pad 151c, which is configured to come into contact with the nose N of the user U1 as illustrated in the lower section of FIG. 11. That is, the nose pad 151c of the glasses 151 comes into contact with the nose (frontal region) N of the user U1, the ear hooks 153 come into contact with the ears (temporal region) E, the occipital region upper portion fixing unit 152 comes into contact with an occipital region upper portion (upper portion when viewed from the occipital region and part close to the crown) of the head of the user U1, and the occipital region fixing unit 154 comes into contact with the occipital region.

Therefore, the mounting tool 141 is fixed in contact with the nose (frontal region), the ears (temporal region), the occipital region upper portion, and the occipital region of the head of the user U1, and it therefore becomes possible to suppress occurrence of displacement of the mounting tool 141 accompanied by movement of the head of the user U1 due to the weight of the sensor device 10A and to maintain a stable fixed state even when the sensor device 10F is mounted on the bracket 155.

Moreover, the insertion portions 152a and 153a each include a flexible material, and when the temple 151b is inserted, the insertion portions 152a and 153a are deformed to enable insertion and are set into a state where the temple 151b is inserted to a predetermined insertion depth, so that the temple 151b is fixed at a predetermined insertion depth set by the temple 151b by sandwiching the temple 151b by the restoring force (contraction force) of the shapes of the insertion portions 152a and 153a.

In this way, the temple 151b inserted into the insertion portions 152a and 153a is fixed at a predetermined insertion depth, so that it is possible to adjust contact pressure to the frontal region toward the center of the head via the nose pad 151c of the glasses 151 and the contact pressure to the occipital region toward the center of the head by the occipital region fixing unit 154.

That is, the glasses 151, the ear hooks 153, and the occipital region fixing unit 154 make it possible to suppress occurrence of displacement of the mounting tool 141 in the horizontal and perpendicular directions with respect to the head accompanied by movement of the head due to the weight of the sensor device 10F.

Furthermore, the occipital region upper portion fixing unit 152 makes it possible to suppress occurrence of downward displacement of the mounting tool 141 in the perpendicular direction accompanied by movement of the head due to the weight of the sensor device 10F.

By mounting the sensor device 10F on the head of the user U1 using such a mounting tool 141, the user U1 can wear the sensor device on the head by adjusting the insertion depth of the temple 151b with respect to the insertion portions 152a and 153a so as to appropriately suppress displacement accompanied by movement of the head due to the weight of the sensor device 10F while adjusting the insertion depth into an appropriate state that is neither too tight nor too loose to the head.

As a result, even when the sensor device 10F is mounted on the bracket 155, it becomes possible to suppress occurrence of displacement of the mounting tool 141 accompanied by movement of the head of the user U1 due to the weight of the sensor device 10F without impairing the wearing feeling or the appearance and to mount the sensor device 10F on the head in a stable state, and it becomes possible to appropriately sense the position or the orientation of the head.

Moreover, as illustrated in the lower section of FIG. 11, substantially only the frame 151a of the glasses 151 can be seen in a case where the user U1 wearing the sensor device 10F mounted by the mounting tool 141 is viewed from the front direction, and therefore it is unlikely to be recognized that the sensor device 10F is mounted on the head, and it becomes possible to stylishly mount the sensor device 10F on the head with natural appearance.

Although the occipital region upper portion fixing unit 152, the ear hooks 153, and the occipital region fixing unit 154 may be configured not to have flexibility specially, note that it is desirable that the units each include a material having flexibility enough to cause no pain at various contact sites of the head.

Furthermore, the occipital region upper portion fixing unit 152, the ear hooks 153, and the occipital region fixing unit 154 may each include a stretchable material such as a rubber band, for example, so that the contraction force of the material applies pressure to come into contact with the frontal region, the temporal region, the occipital region upper portion, and the occipital region, and fixes the mounting tool 141 to the head.

Moreover, although the above description has explained an example in which the mounting tool 141 includes the glasses 151, the occipital region upper portion fixing unit 152, the ear hooks 153, the occipital region fixing unit 154, and the bracket 155, the mounting tool 141 may include the glasses 151, the ear hooks 153, the occipital region fixing unit 154, and the bracket 155 excluding the occipital region upper portion fixing unit 152 in a case where it is expected in advance that the user U1 does not move violently. In this case, the temple 151b of the glasses 151 is inserted only into the insertion portions 153a of the ear hooks 153. That is, the temple 151b is not inserted into the insertion portions 152a because of the configuration that the occipital region upper portion fixing unit 152 is not provided.

By inserting the temple 151b of the glasses 151 into the insertion portions 153a of the ear hooks 153, the glasses 151, the ear hooks 153, and the occipital region fixing unit 154 form an annular structure surrounding the head of the user U1 so that pressure is applied toward the center of the head in a state where the nose (frontal region) is in contact with the nose pad 151c of the glasses 151, the ears (temporal region) are in contact with the ear hooks 153, and the occipital region is in contact with the occipital region fixing unit 154, and it is therefore also possible in such a configuration to support the weight of the bracket 155 and the sensor device 10F as long as the head does not move violently.

6. Configuration Example of Insertion Portion

<6-1. First Configuration Example of Insertion Portion>

Next, the configurations of the insertion portions 152a and 153a will be described.

The insertion portions 152a and 153a need to have a configuration in which the temple 151b of the glasses 151 can be inserted (inserted and removed), and the temple 151b can be fixed in a state of being inserted into the insertion portions 152a and 153a.

Figure 13:
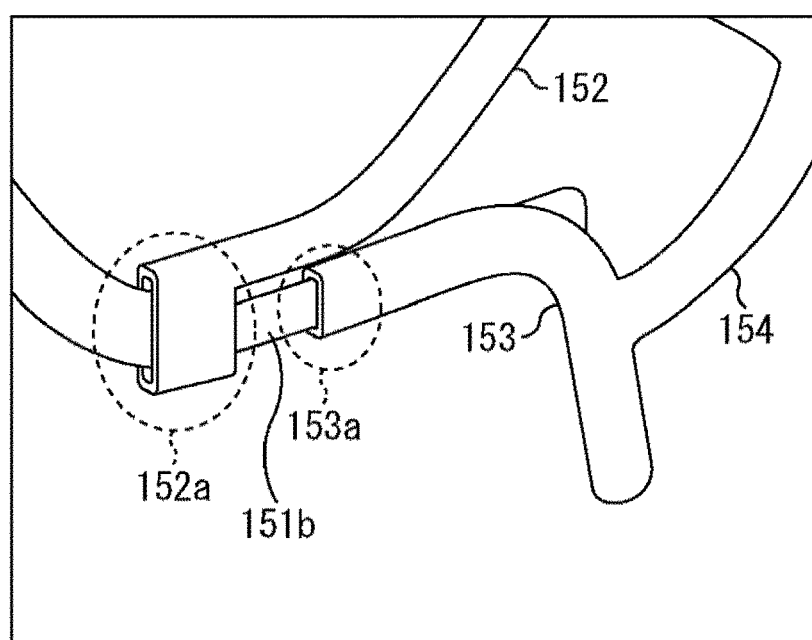
FIG. 13 is a view illustrating a first configuration example of an insertion portion.

Accordingly, as illustrated in FIG. 13, for example, it is preferable that the insertion portions 152a and 153a each include a material having flexibility enough to allow the insertion portions to be deformed to the extent that the temple 151b can be inserted and removed, and stretchability enough to allow the insertion portions to have contraction force enough to fix the temple 151b to the extent that the temple 151b is not displaced after being inserted.

Since it is desirable that the insertion portions 152a and 153a each include a material having such characteristics, it is desirable that the insertion portions 152a and 153a include, for example, a thermoplastic elastomer, silicone rubber, natural rubber, or the like.

Furthermore, in the case of FIG. 13, the insertion portions 152a and 153a need to have flexibility enough to allow the temple 151b to be inserted and removed, and stretchability enough to fix the temple 151b to the extent that the temple 151b is not displaced, and therefore the openings of the insertion portions 152a and 153a are each formed to have a size corresponding to the thickness (diameter) of the temple 151b.

<6-2. Second Configuration Example of Insertion Portion>

Although the above description has explained an example in which the insertion portions 152a and 153a are configured to have flexibility enough to allow the temple 151b to be inserted, and stretchability enough to fix the inserted temple 151b to the extent that the temple 151b is not displaced, the temple 151b may be configured to be inserted (inserted and removed) and fixed to the extent that the temple is not displaced by virtue of the shape.

Figure 14:
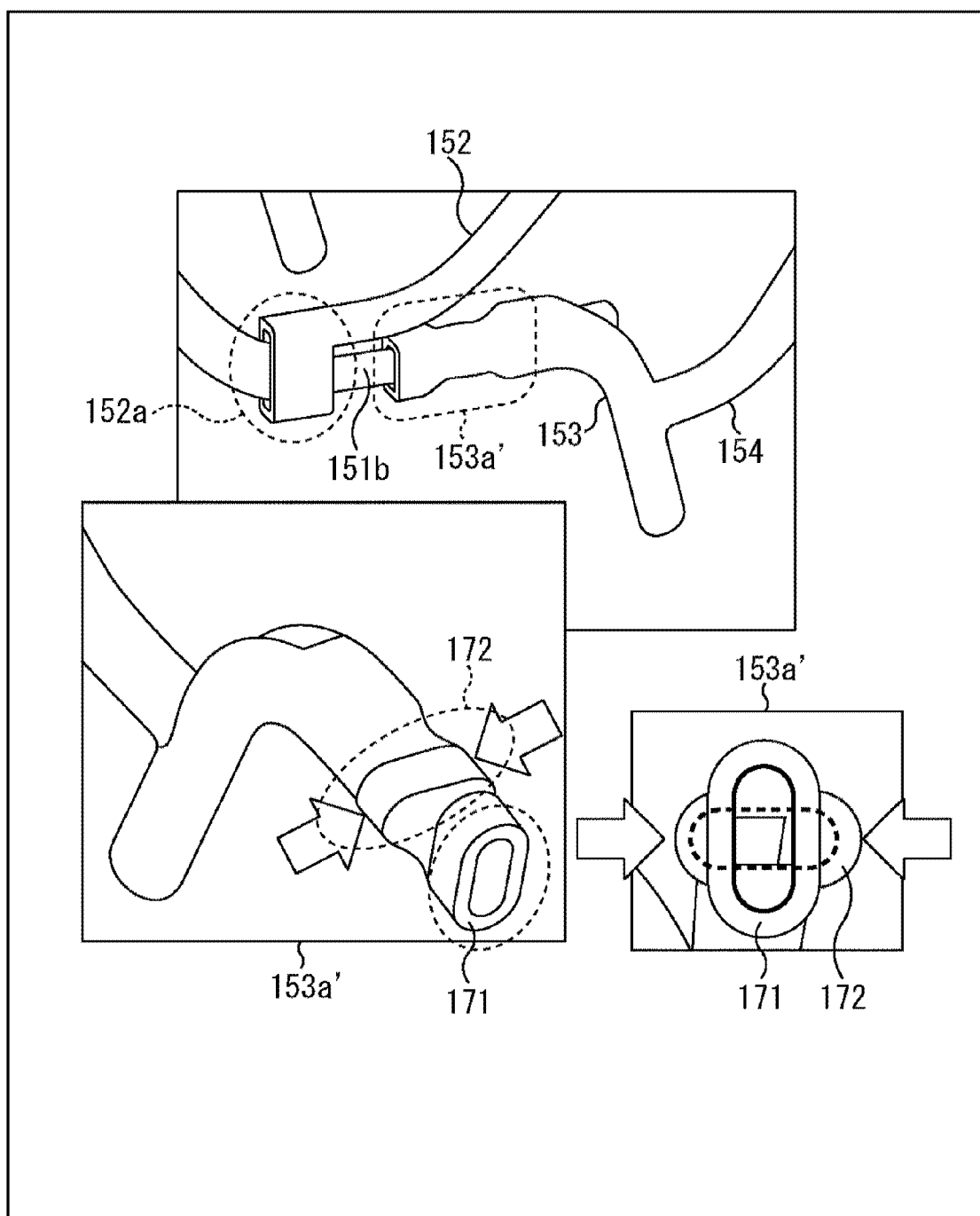
FIG. 14 is a view illustrating a second configuration example of an insertion portion.

FIG. 14 illustrates a configuration example of an insertion portion 153a in which the shape of the insertion portion allows the temple 151b to be inserted (inserted and removed) and fixed to the extent that the temple is not displaced. In FIG. 14, note that the insertion portion 152a is the same as that of FIG. 13.

An insertion portion 153a' of FIG. 14 includes two elliptical portions 171 and 172 in which the major axis of an opening is deviated by 90 degrees due to a flexible material.

Here, the size of the major axis of the elliptical portions 171 and 172 is larger than the diameter of the temple 151b, and the size of the minor axis is smaller than the diameter of the temple 151b. In FIG. 14, note that the elliptical portion 171 having a major axis formed in the vertical direction is provided at the opening of the insertion portion 153a', and an elliptical portion 172 having a major axis deviated by approximately 90 degrees from the major axis of the elliptical portion 171 is provided in the back section of the elliptical portion 171. However, front or back of the elliptical portions 171 and 172 may be interchanged.

Although both the elliptical portions 171 and 172 each include a flexible material, since the elliptical portions have a fixed shape, the minor axis portion can be expanded and the temple 151b can be inserted by pressing the major axis part of the elliptical portion 172 by pinching in the arrow direction of FIG. 14 when the temple 151b is inserted.

Furthermore, after the temple 151b is inserted to an appropriate insertion depth, pressing the elliptical portion 172 by pinching is released, so that the temple 151b is sandwiched and fixed by the restoring force (contraction force) of the elliptical portion 172 to return to the original shape thereof.

That is, the insertion portion 153' of FIG. 14 makes it possible to insert (insert and remove) the temple 151b and fix the temple to the extent that the temple is not displaced, and as a result, the sensor device 10F can be appropriately fixed to the head of the user U1 by the mounting tool 141.

<6-3. Third Configuration Example of Insertion Portion>

Although the above description has explained an example in which the temple 151b can be inserted (inserted and removed) and fixed to the extent that the temple is not displaced by virtue of the material and the shape of the insertion portions 152a and 153a, a lock mechanism may be added to the insertion portions 152a and 153a.

Figure 15:
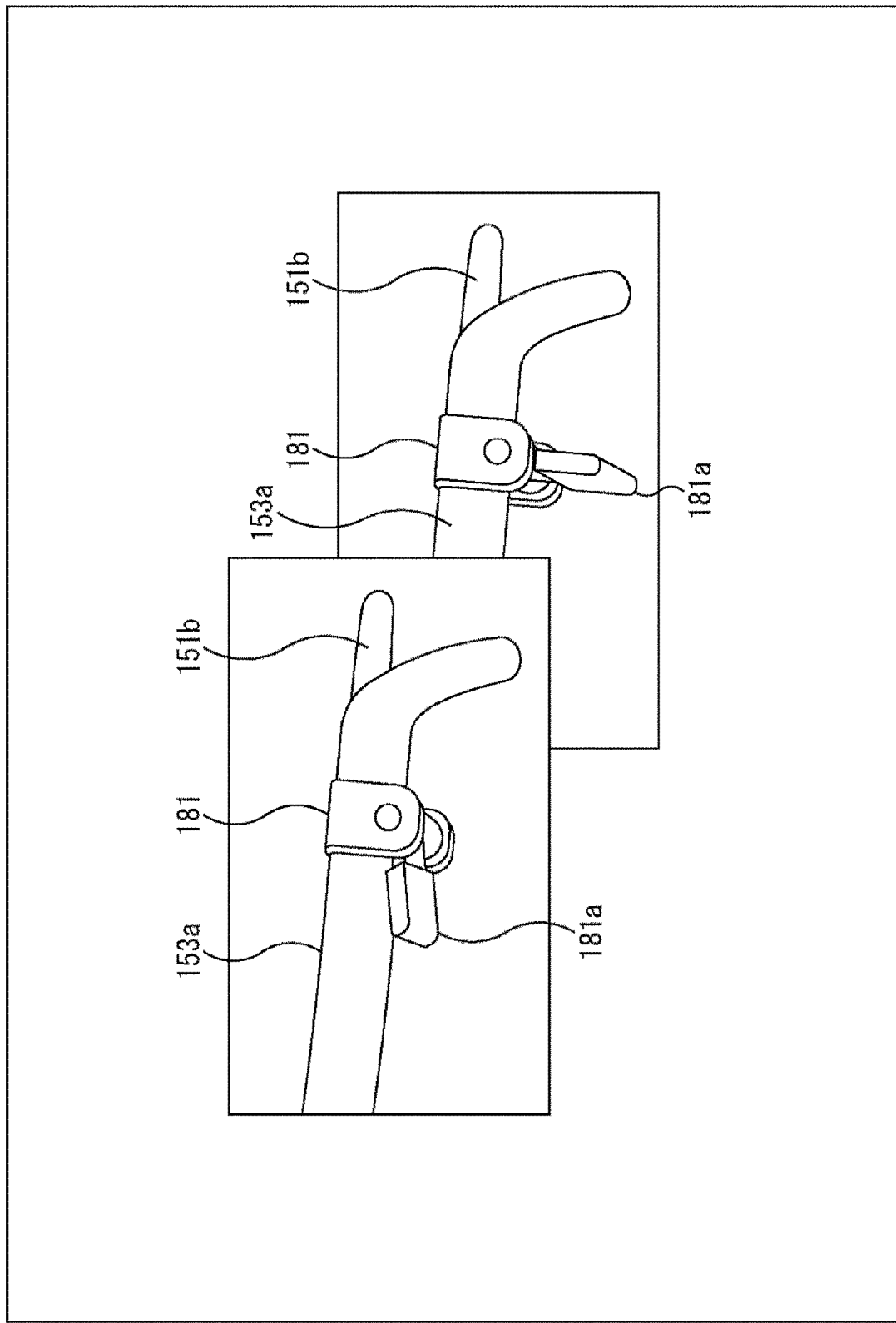
FIG. 15 is a view illustrating a third configuration example of an insertion portion.

That is, for example, a lock mechanism 181 illustrated in FIG. 15 may be configured on the outer peripheral portion of the insertion portion 153a. Note that FIG. 15 is an external perspective view of the lock mechanism 181.

As illustrated in FIG. 15, the lock mechanism 181 is wound around the outer peripheral portion of the insertion portion 153a, and the temple 151b can be inserted (inserted and removed) when a lever 181a is erected at 90 degrees with respect to the insertion direction of the insertion portion 153a as illustrated in the right part of FIG. 15, or the temple 151b can be fixed to the extent that the temple is not displaced when the lever 181a is tilted so as to be parallel to the insertion direction as illustrated in the left part of FIG. 15.

Figure 16:
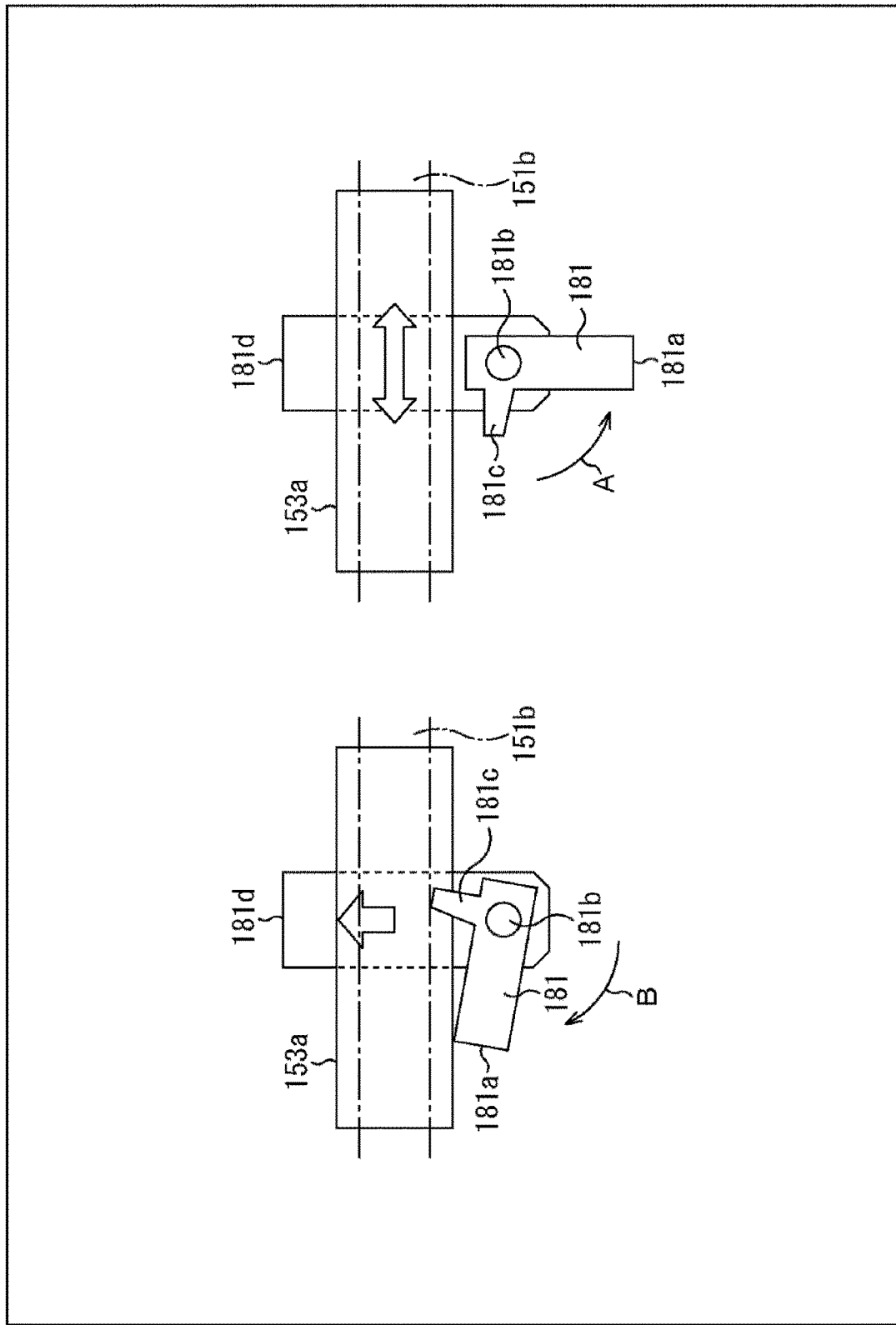
FIG. 16 is a diagram illustrating a detailed structure of a third configuration example of an insertion portion.

More specifically, as illustrated in FIG. 16, the lock mechanism 181 includes the lever 181a, a shaft 181b, a claw 181c, and a holder 181d. Then, in the lock mechanism 181, the holder 181d is wound around the outer peripheral portion of the insertion portion 153a, and the shaft 181b that can rotate the lever 181a in the direction of arrow A or arrow B in FIG. 16 with respect to the direction in which the holder 181d is wound is provided. Moreover, the lever 181a is provided with the claw 181c that is formed on the shaft 181b to have 90 degrees with respect to the longitudinal direction of the lever 181a.

With such a configuration, when the lever 181a is rotated in the direction of arrow A as illustrated in the right part of FIG. 16, the claw 181c is not in contact with the insertion portion 153a, so that the inside of the insertion portion 153a becomes loose and the temple 151b can be inserted and removed. Therefore, the temple 151b is inserted into the insertion portion 153a to a position of an appropriate insertion depth in this state.

Then, when the temple 151b is inserted into the insertion portion 153a to an appropriate insertion depth and the lever 181a is rotated in the direction of arrow B as illustrated in the left part of FIG. 16, the claw 181c comes into contact with the insertion portion 153a and the temple 151b inserted into the insertion portion 153a is pressed, and therefore the temple 151b can be fixed in the insertion portion 153a so that the temple cannot be inserted or removed.

By providing such a lock mechanism 181 and rotating the lever 181a, the temple 151b can be fixed in the insertion portion 153a, and as a result, the sensor device 10F can be appropriately fixed to the head of the user U1 by the mounting tool 141.

7. Modified Example of Occipital Region Upper Portion Fixing Unit

Next, a modified example of the occipital region upper portion fixing unit 152 will be described.

Figure 17:
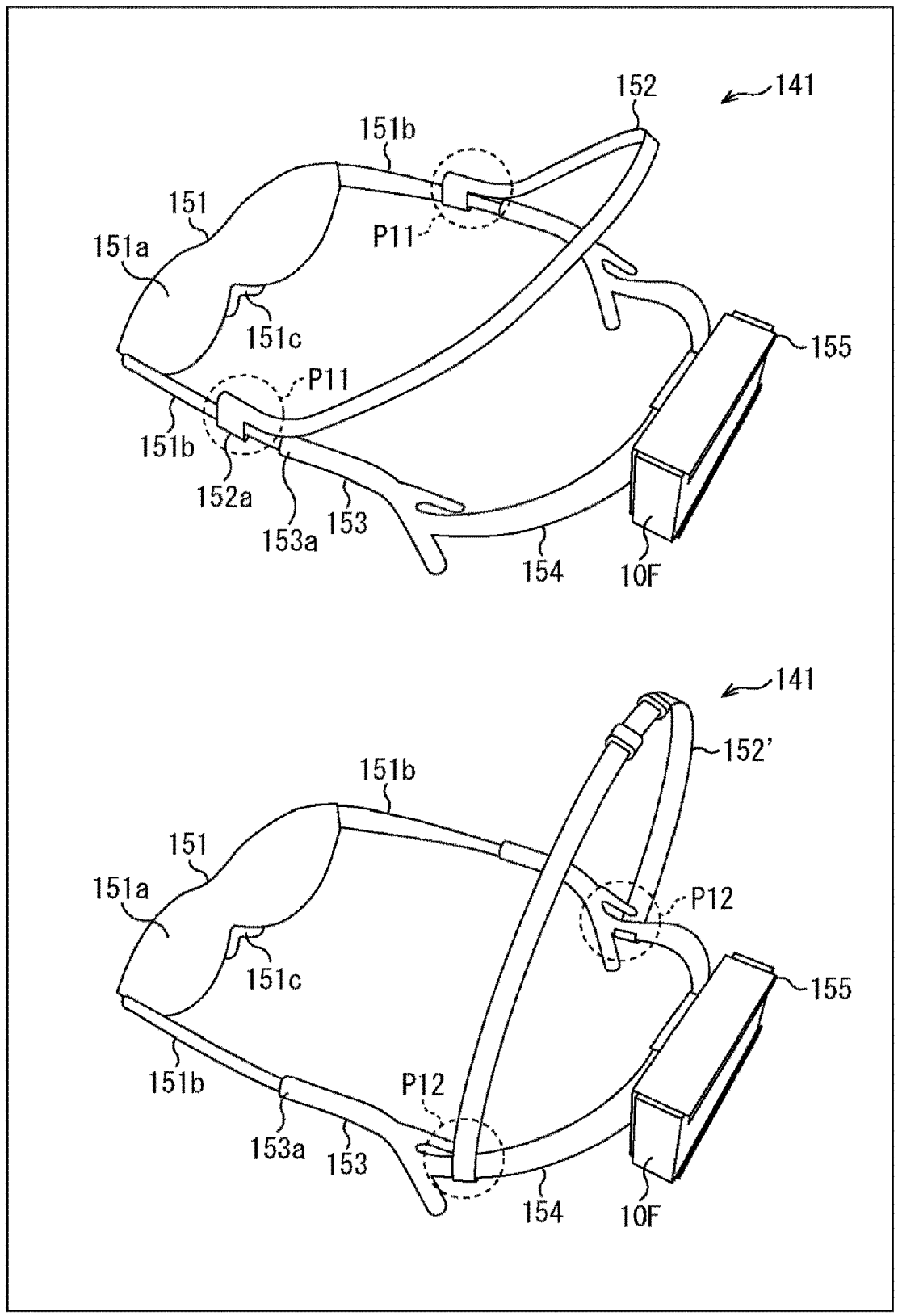
FIG. 17 is a view illustrating a modified example of an occipital region upper portion fixing unit.

As illustrated in the upper section of FIG. 17, the occipital region upper portion fixing unit 152 of FIG. 11 or 12 is configured to come into contact with and fix areas of the ear hooks 153 from front step parts P11 of the insertion portions 153a of the ear hooks 153, which are on the side of the glasses 151, to the occipital region upper portion in a band shape. However, other configurations may be employed as long as the glasses 151 and any site of an annular structure that includes the ear hooks 153 and the occipital region fixing unit 154 and passes through the frontal region, the temporal region, and the occipital region can support a part of load in the vertical direction at the occipital region upper portion.

For example, as illustrated by an occipital region upper portion fixing unit 152' in the lower section of FIG. 17, an area from the back step parts P12 of the ear hooks 153, which are sites close to the ear hooks 153 on the side of the occipital region upper portion fixing unit 154, may be fixed to come into contact in a band shape.

That is, since the mounting tool 141 illustrated in the lower section of FIG. 17 is also fixed in contact with the nose (frontal region), the ears (temporal region), the occipital region upper portion, and the occipital region of the head of the user U1, it becomes possible to suppress occurrence of displacement accompanied by movement of the head of the user U1 due to the weight of the sensor device 10F and to mount the sensor device 10F on the head in a stable state even when the sensor device 10F is mounted on the bracket 155.

8. Modified Example of Configuration that Comes into Contact with Frontal Region <8-1. Configuration Example that Comes into Contact with the Entire Surface of Forehead>

The above description has explained an example in which a configuration that the nose pad 151c of the glasses 151 comes into contact with the nose (frontal region) of the user U1, and the temple 151b is inserted into the insertion portions 152a of the occipital region upper portion fixing unit 152 in the front section of the ear hooks 153 and is then inserted into the insertion portions 153a to form an annular structure that comes into contact with the frontal region, the temporal region, and the occipital region as illustrated in FIGS. 11 and 12, and moreover, by fixing an occipital region upper portion by the occipital region upper portion fixing unit 152, contact pressure toward the head center is applied from the frontal region, the occipital region, and the occipital region upper portion, so that the sensor device 10F is mounted on the head of the user U1 in a stable state using the mounting tool 141.

However, since it is only required that the entire of the mounting tool 141 is fixed in contact with the frontal region, the temporal region, and the occipital region, and is further fixed in contact with the occipital region upper portion, a configuration that comes into contact with the frontal region may be a configuration other than the glasses 151.

For example, a configuration in which a band-type configuration comes into contact with the frontal region may be provided instead of the glasses 151.

Figure 18:
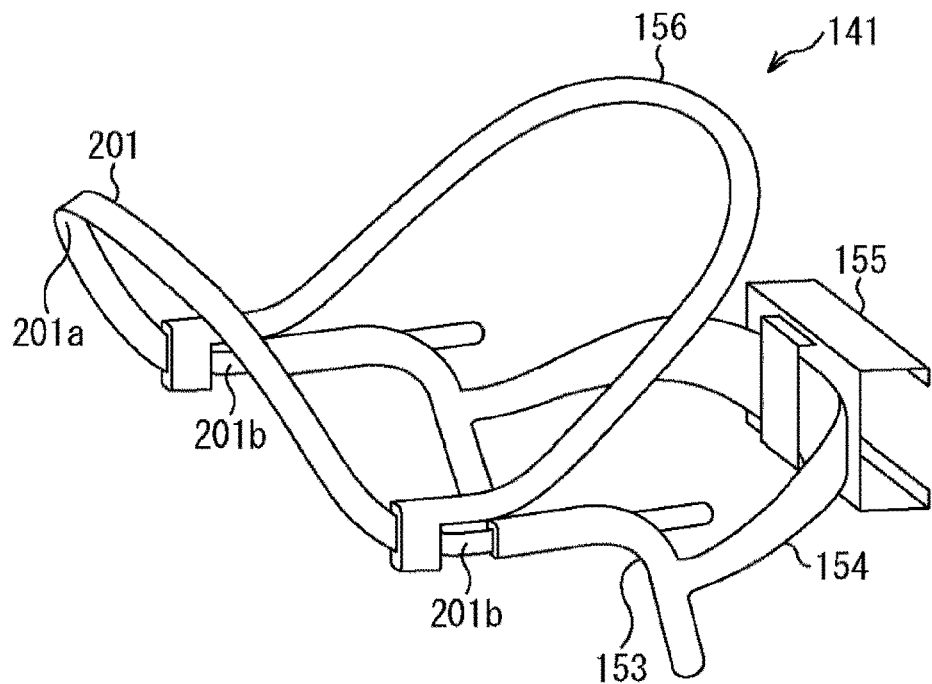
FIG. 18 is a view illustrating a modified example of the configuration of the frontal region that comes into contact with the entire surface of the forehead.

FIG. 18 illustrates a configuration example of a mounting tool 141 in a case where a frontal region fixing band 201 in which a band-type configuration comes into contact with the frontal region is provided instead of the glasses 151.

The frontal region fixing band 201 includes a band portion 201a that comes into contact with the forehead part of the user U1, and insertion rod portions 201b that are inserted into the insertion portions 152a of the occipital region upper portion fixing unit 152, and the insertion portions 153a of the ear hooks 153.

That is, the band portion 201a of the frontal region fixing band 201 has a configuration corresponding to the nose pad 151c in the glasses 151, and the band portion 201a fixes the mounting tool 141 to the frontal region with the band-shaped configuration coming into contact with the entire forehead, while the nose pad 151c comes into contact with the nose of the user U1 so that the mounting tool 141 is fixed to the frontal region.

Furthermore, the insertion rod portions 201b have a configuration corresponding to the temple 151b of the glasses 151, and are inserted into the insertion portions 152a of the occipital region upper portion fixing unit 152, and the insertion portions 153a of the ear hooks 153.

Therefore, since the mounting tool 141 is fixed in contact with each of the forehead (frontal region), the ears (temporal region), the occipital region upper portion, and the occipital region of the head of the user U1, it becomes possible to suppress occurrence of displacement of the mounting tool 141 accompanied with movement of the head of the user U1 due to the weight of the sensor device 10F and to mount the sensor device 10F on the head of the user U1 in a stable state even when the sensor device 10F is mounted on the bracket 155.

Furthermore, the contact pressure to the forehead (frontal region) by the band portion 201a of the frontal region fixing band 201 and the contact pressure to the occipital region by the occipital region fixing unit 154 can be adjusted using the insertion depth of the insertion rod portions 201b inserted into the insertion portions 152a and 153a, and as a result, it is possible to appropriately mount the sensor device 10F by the mounting tool 141 while adjusting the head of the user U1 to an appropriate state that is neither too tight nor too loose.

<8-2. Application Example of Configuration that Comes into Contact with the Entire Forehead so as to Fix Frontal Region>

Although the above description has explained an example in which the frontal region fixing band 201 in the mounting tool 141 is used as a configuration for fixing the frontal region, when a user U1 with long hair or the like tries to wear the mounting tool 141 of FIG. 18 in the case of such a configuration, the user has to pass a part, which is an annular structure including the frontal region fixing band 201, the ear hooks 153, and the occipital region fixing unit 154, to the neck, rake out hair from the annular part, and then lift the annular part to the mounting position.

That is, mounting is troublesome for a user U1 with long hair in the case of the configuration illustrated in FIG. 18. Therefore, the frontal region fixing band 211 may have a configuration in which a part of the annular structure can be opened and closed for mounting.

Figure 19:
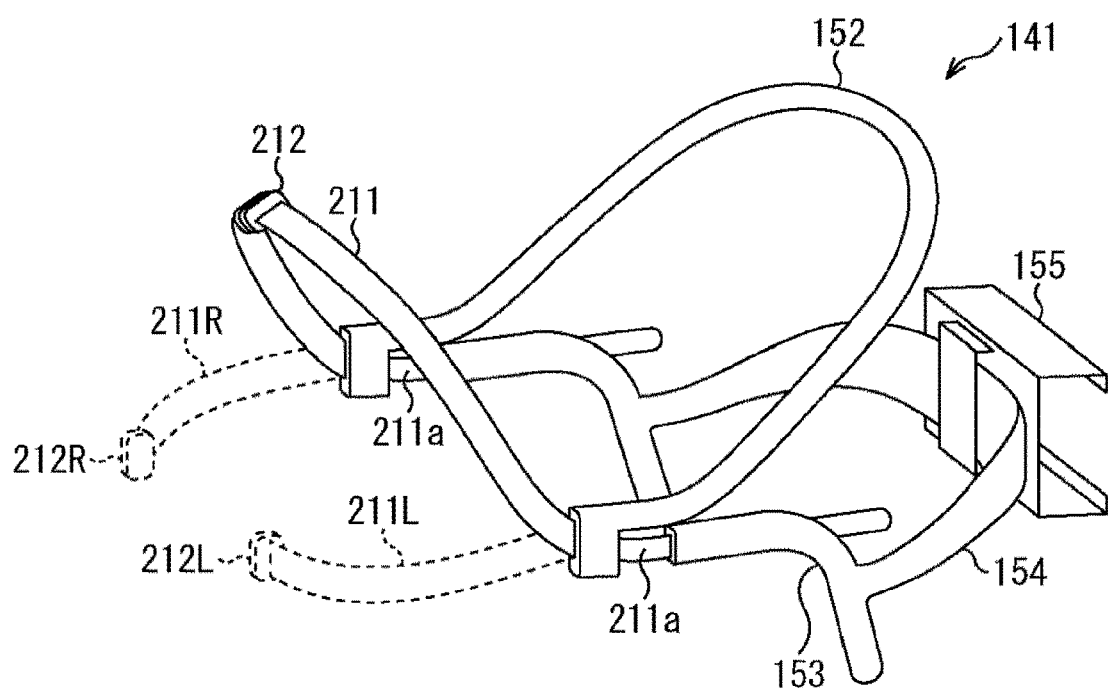
FIG. 19 is a view illustrating an application example of the configuration of the frontal region that comes into contact with the entire surface of the forehead.

FIG. 19 illustrates a configuration example of a mounting tool 141 in which a frontal region fixing band 211 including a highly flexible material is provided instead of the frontal region fixing band 201.

The frontal region fixing band 211 is provided with a detachable portion 212, which can be detached, at a site of the frontal region fixing band 201 that comes into contact with the front forehead. Furthermore, the frontal region fixing band 211 is provided with insertion rod portions 211a, which have a function similar to the temple 151b.

More specifically, the detachable portion 212 can be divided into a left detachable portion 212L and a right detachable portion 212R and be detached. Accordingly, by separating the left detachable portion 212L and the right detachable portion 212R at the time of mounting, the frontal region fixing band 211 is divided into the left band portion 211L and the right band portion 211R, and therefore this example is released from the above-mentioned annular structure. Accordingly, the mounting tool 141 can be mounted by passing the neck between both the left detachable portion 212L and the right detachable portion 212R, hanging the occipital region fixing unit 154 on the neck, then lifting the left detachable portion 212L and the right detachable portion 212R from under hair to the forehead, and connecting the left detachable portion 212L and the right detachable portion 212R of the detachable portion 212.

With such a configuration, since even a user with long hair does not have to put a part, which is an annular structure formed by the mounting tool 141, over the head, pass the part to the neck, and then scrape out hair from the part, which is an annular structure, at the time of mounting the mounting tool 141, it becomes easy to mount the mounting tool 141. Furthermore, in a case where the mounting tool 141 is detached in a similar manner, the detachable portion 212 can be divided into the left detachable portion 212L and the right detachable portion 212R and detached after being displaced to be hung on the neck, and therefore even a user U1 with long hair also can easily detach the mounting tool 141.

<8-3-1. Configuration Example 1 that Comes into Contact with a Part of Forehead>

Although the above description has explained an example of fixing the frontal region by coming into contact with the entire surface of the forehead using the frontal region fixing bands 201 and 211 as a configuration for fixing the frontal region, a configuration that comes into contact with not the entire forehead but a part of the forehead may be employed as long as the configuration can fix the frontal region.

Figure 20:
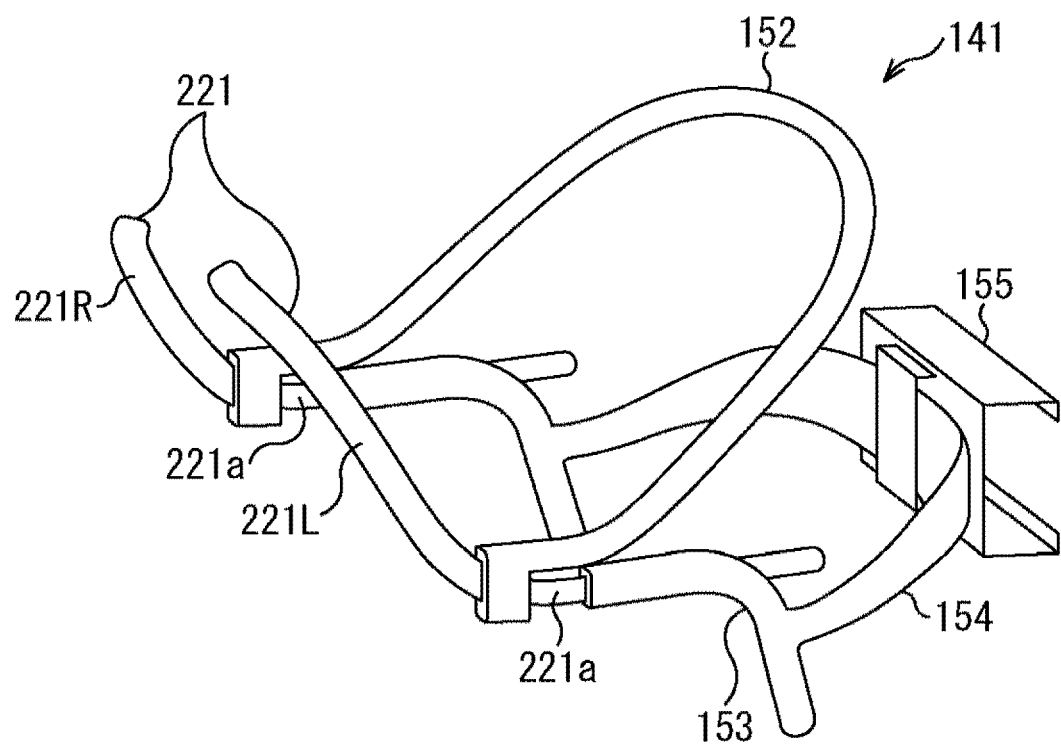
FIG. 20 is a view illustrating Modified Example 1 of the configuration of the frontal region that comes into contact with a part of the forehead.

FIG. 20 is a configuration example of a mounting tool 141 in which a frontal region fixing unit 221 is provided instead of the frontal region fixing bands 201 and 211 of FIGS. 18 and 19.

Although the frontal region fixing bands 201 and 211 are configured to come into contact with the entire forehead and fix the frontal region, the frontal region fixing unit 221 includes a member having no stretchability and low flexibility, includes a left frontal region fixing unit 221L and a right frontal region fixing unit 221R, and comes into contact with the left side and the right side of the forehead in the frontal region, respectively. Furthermore, the frontal region fixing unit 221 is provided with insertion rod portions 221a, which have a function similar to the temple 151b.

Regarding the mounting tool 141 including the frontal region fixing band 201 or 211, the ear hooks 153, and the occipital region fixing unit 154, an annular structure surrounding the head when the head of the user U1 is viewed from above fixes the mounting tool 141 to the head.

However, regarding the mounting tool 141 of FIG. 20, the left frontal region fixing unit 221L constituting the frontal region fixing unit 221 comes into contact with the left side of the forehead, and the right frontal region fixing unit 221R constituting the frontal region fixing unit 221 comes into contact with the right side of the forehead, so that the frontal region is fixed in a state where the front part of the forehead is not in contact with any of the units.

That is, although the mounting tool 141 of FIG. 20 does not have an annular structure when the head of the user U1 is viewed from above, the frontal fixing unit 221 includes a hard member having no stretchability and low flexibility, so that the left frontal region fixing unit 221L and the right frontal region fixing unit 221R come into contact with the left and right parts of the forehead, respectively, so as to fix the frontal region, the temporal region, the occipital region upper portion, and the occipital region as a whole.

In the mounting tool 141 having the configuration illustrated in FIG. 20, the left occipital region fixing unit 221L and the right occipital region fixing unit 221R respectively come into contact with and fix the left forehead and the right forehead, the ear hooks 153 come into contact with and fix the temporal region, the occipital region upper portion fixing unit 152 comes into contact with and fixes the occipital region upper portion, and the occipital region fixing unit 154 comes into contact with and fixes the occipital region, and it therefore becomes possible to suppress occurrence of displacement of the mounting tool 141 accompanied by movement of the head of the user U1 due to the weight of the sensor device 10F and to mount the sensor device 10F on the head of the user U1 in a stable state.

<8-3-2. Configuration Example 2 that Comes into Contact with a Part of Forehead>

Although the above description has explained a configuration example of the mounting tool 141 of FIG. 20 in which the frontal region fixing unit 221 is provided instead of the frontal region fixing bands 201 and 211 of FIGS. 18 and 19, moreover, the frontal region fixing unit 221, the occipital region upper portion fixing unit 152, the ear hooks 153, and the occipital region fixing unit 154 may be integrated.

Figure 21:
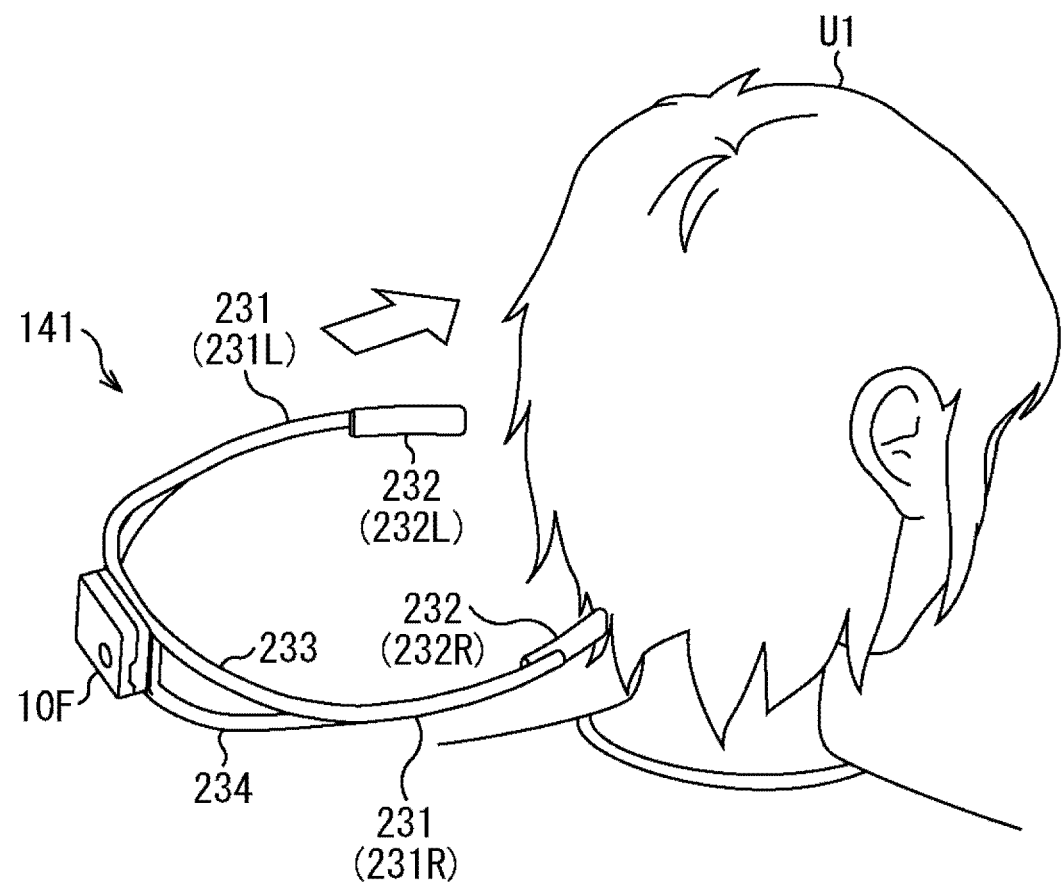
FIG. 21 is a view illustrating Modified Example 2 of the configuration of the frontal region that comes into contact with a part of the forehead.
Figure 22:
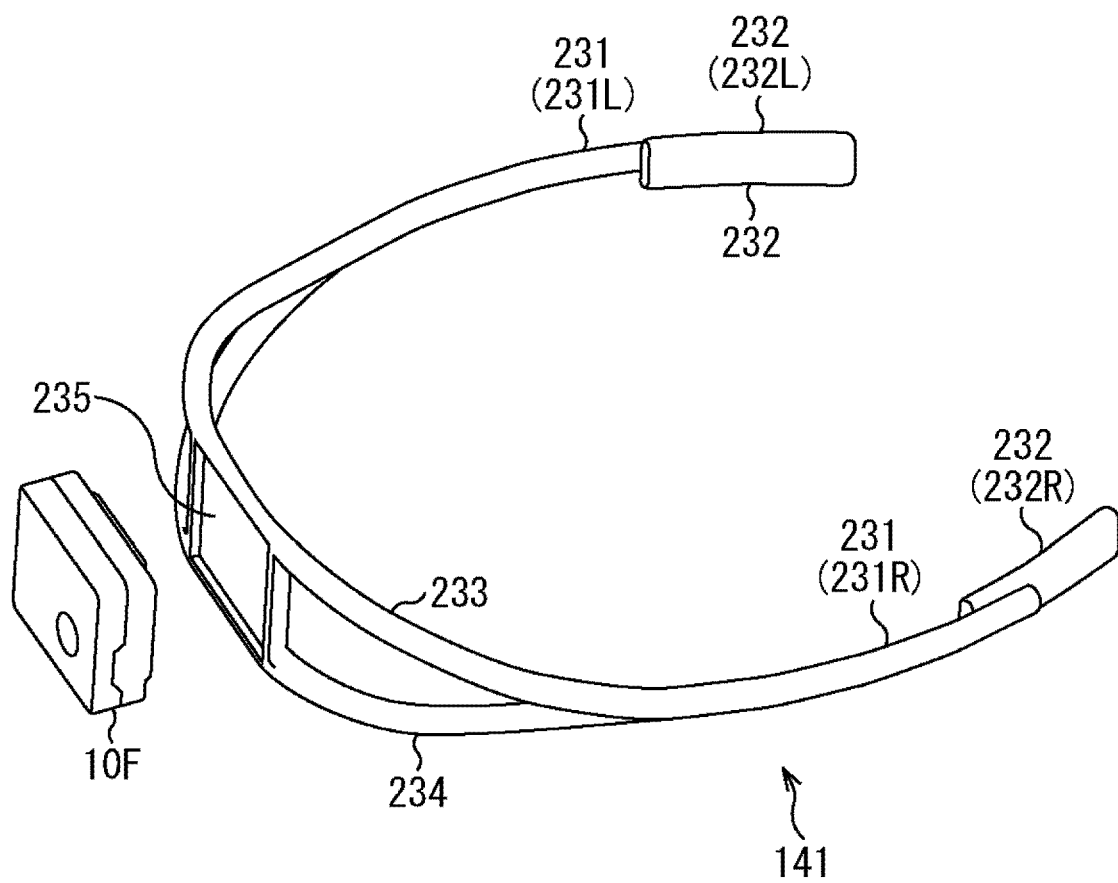
FIG. 22 is a view illustrating Modified Example 2 of the configuration of the frontal region that comes into contact with a part of the forehead.
Figure 23:
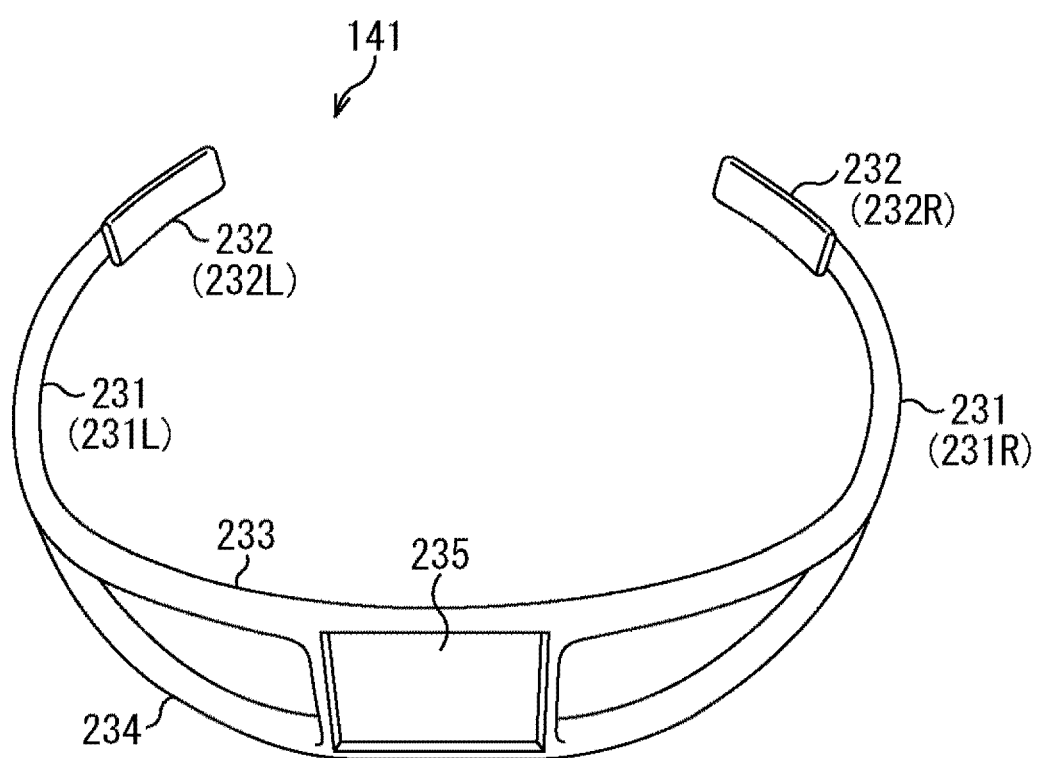
FIG. 23 is a view illustrating Modified Example 2 of the configuration of the frontal region that comes into contact with a part of the forehead.

FIG. 21 is a configuration example of a mounting tool 141 in which the frontal region fixing unit 221, the occipital region upper portion fixing unit 152, the ear hooks 153, and the occipital region fixing unit 154 are integrated. Note that FIG. 22 illustrates an exploded view of the mounting tool 141 of FIG. 21, and FIG. 23 illustrates an external view of a state where the sensor device 10F is detached from the mounting tool 141, viewed from the occipital region side.

More specifically, in the mounting tool 141 of FIG. 21, the frontal region fixing unit 231, the occipital region upper portion fixing unit 233, and the occipital region fixing unit 234 are configured integrally.

Here, the frontal region fixing unit 231 of FIG. 21 has a configuration corresponding to the frontal region fixing unit 221 of FIG. 20, and includes a left frontal region fixing unit 231L and a right frontal region fixing unit 231R.

The left and right tip portions of the frontal region fixing unit 231 are provided with contact portions 232 that come into contact with the forehead of the head of the user U1, and the tip portions of a left frontal region fixing unit 231L and a right frontal region fixing unit 231R are respectively provided with a left frontal region contact portion 232L and a right frontal region contact portion 232R.

Furthermore, the frontal region fixing unit 231 of FIG. 21 also has a function of the ear hooks 153 in FIG. 20, and is fixed in contact with the temporal region.

Moreover, an occipital region upper portion fixing unit 233 configured integrally with the frontal region fixing unit 231, and an occipital region fixing unit 234 are provided on the occipital region side and have a function respectively corresponding to the occipital region upper portion fixing unit 152 and the occipital region fixing unit 154.

Furthermore, in the mounting tool 141 of FIG. 21, an adhesion surface 235 is provided to come into contact with and fix the sensor device 10F formed to straddle the occipital region upper portion fixing unit 233 and the occipital region fixing unit 234 as illustrated in FIGS. 22 and 23.

That is, in the mounting tool 141 of FIG. 21, the sensor device 10F is fixed to the adhesive surface 235 in a state of being directly adhered using an adhesive or the like.

Of course, as in the mounting tool 141 in FIG. 20, a bracket 155 may be formed to straddle the occipital region upper portion fixing unit 233 and the occipital region fixing unit 234, so that the sensor device 10F has a detachable configuration.

The frontal region fixing unit 231 in FIG. 21 includes a member having non stretchability and low flexibility and includes the left frontal region fixing unit 231L and the right frontal region fixing unit 231R on each of the left and right sides, and the left frontal region contact portion 232L and the right frontal region contact portion 232R of the respective tip portions come in contact with the left and right sides of the forehead of the frontal region. The member of the frontal region fixing unit 231 may be thermoplastic elastomer, silicone rubber, natural rubber, or the like, or may be general resin such as polycarbonate, ABS resin, or acrylic.

Regarding the mounting tool 141 of FIG. 21, the left side of the forehead also comes into contact with the left frontal region contact portion 232L of the left frontal region fixing unit 231L constituting the frontal fixing unit 231 and the right side of the forehead also comes into contact with the right frontal region contact portion 232R of the right frontal region fixing unit 231R constituting the frontal region fixing unit 231, so that the frontal region is fixed in a state where the front part of the forehead is not in contact with any of the contact portions.

Figure 24:
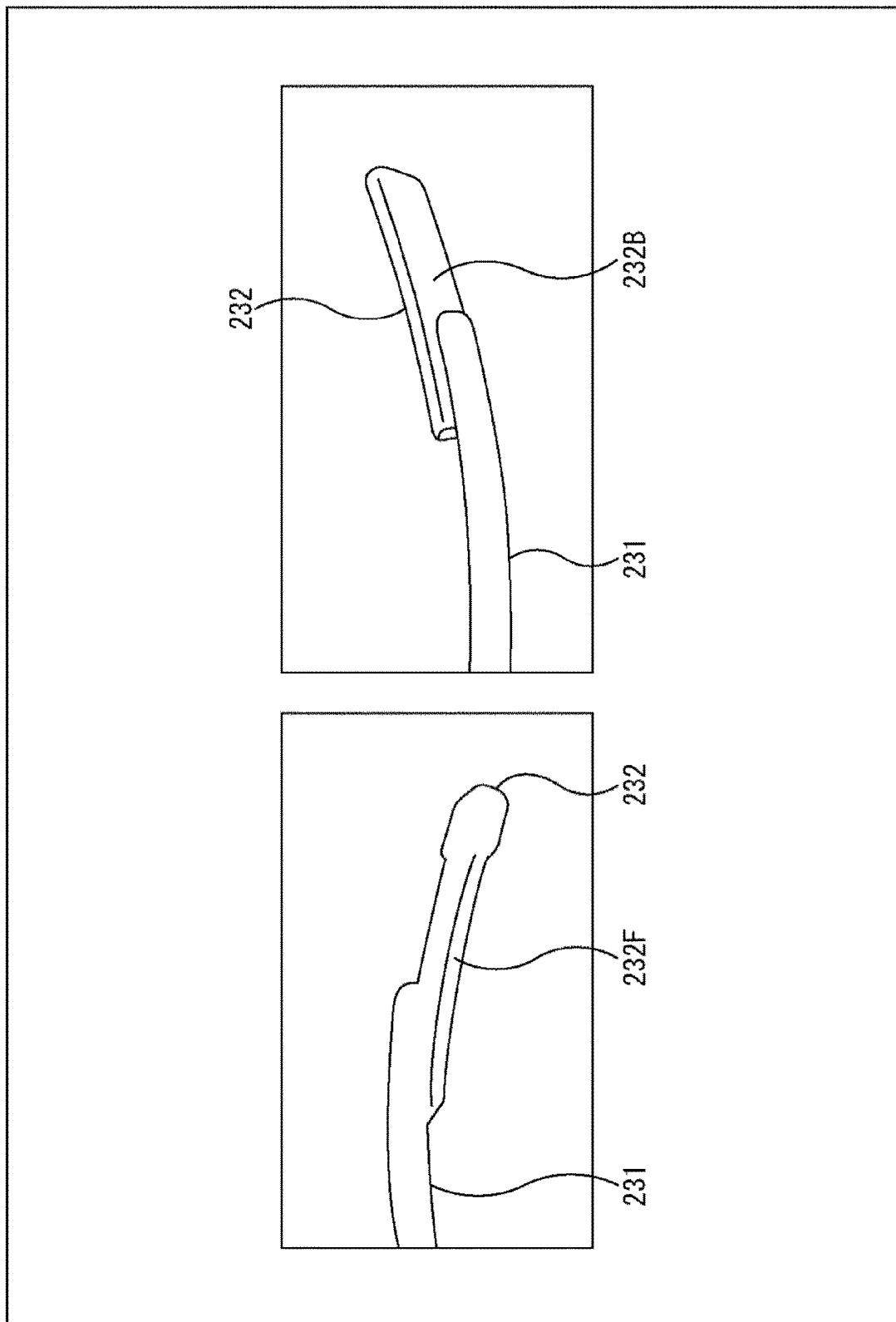
FIG. 24 is a view illustrating the configuration of a contact portion of FIG. 21.

More specifically, as illustrated on the left part of FIG. 24, a front surface 232F of the contact portion 232 that comes into contact with the forehead has a bent structure corresponding to the shape of the forehead, and has a shape that comes into contact with the forehead in an appropriately close contact. Furthermore, as illustrated on the right part of FIG. 24, the back surface 232B that does not come into contact with the forehead of the contact portion 232 has a bent shape corresponding to the front surface 232F.

That is, although the mounting tool 141 of FIG. 21 is not configured to have an annular structure when the head of the user U1 is viewed from above, the frontal fixing unit 231 includes a hard member having no stretchability and low flexibility, so that the left occipital region contact portion 232L of the left occipital region fixing unit 231L and the right occipital region contact portion 232R of the right occipital region fixing unit 221R come into contact with the left and right parts of the forehead, respectively, in a close contact with shapes being matched, so as to fix the frontal region, the temporal region, the occipital region upper portion, and the occipital region as a whole.

In the mounting tool 141 having the configuration illustrated in FIG. 21, the left frontal region contact portion 232L of the left frontal region fixing unit 231L and the right frontal region contact portion 232R of the right frontal region fixing unit 221R respectively come into contact with the left and right foreheads (or temple) and fix the frontal region, the left frontal region fixing unit 231L and the right frontal region fixing unit 221R come into contact with and fix the temporal region, the occipital region upper portion fixing unit 233 comes into contact with and fixes the occipital region upper portion, and the occipital region fixing unit 234 comes into contact with and fixes the occipital region, and therefore it becomes possible to suppress occurrence of displacement of the mounting tool 141 accompanied by movement of the head of the user U1 due to the weight of the sensor device 10F and to mount the sensor device 10F on the head of the user U1 in a stable state.

Furthermore, in the mounting tool 141 of FIG. 21, the glasses 151 of FIG. 11, the occipital region fixing band 201 of FIG. 18, the occipital region fixing band 211 of FIG. 19, or the occipital region fixing unit 221 of FIG. 20, the occipital region upper portion fixing unit 152, the ear hooks 153, and the occipital region fixing unit 154 are not configured as separate bodies but are integrated as the frontal region fixing unit 231, the occipital region upper portion fixing unit 233, and the occipital region fixing unit 234, so that it is unnecessary to adjust the length to be inserted or the like, and mounting becomes easy.

Moreover, with the configuration in which the frontal region fixing unit 231, the occipital region upper portion fixing unit 233, and the occipital region fixing unit 234 are integrated, the mounting tool can be mounted on the head of a user with various hairstyles by mounting from the occipital region. That is, in the case of a hairstyle in which hair is tied collectively in the vicinity of the occipital region, for example, the mounting tool can also be mounted while avoiding the knot.

Furthermore, in the case of the mounting tool 141 of FIG. 21, since the frontal region fixing unit 231, the occipital region upper portion fixing unit 233, and the occipital region fixing unit 234 are integrated, the total area of the components required for mounting is smaller than that of other mounting tools 141, and mounting can be achieved with inconspicuous appearance. Moreover, since the mounting tool can be mounted from the occipital region, the mounting tool can be mounted so as to be hidden under hair in the case of a hairstyle having long hair on the occipital region, for example, and therefore the mounting tool can be mounted with inconspicuous appearance.

<8-4. Application Example of Configuration that Comes into Contact with Frontal Region>

Although the above description has explained an example in which the glasses 151, the frontal region fixing bands 201 and 211, and the frontal region fixing units 221 and 231 are used as a configuration for fixing the frontal region, other configurations may be employed as long as the frontal region can be fixed.

Figure 25:
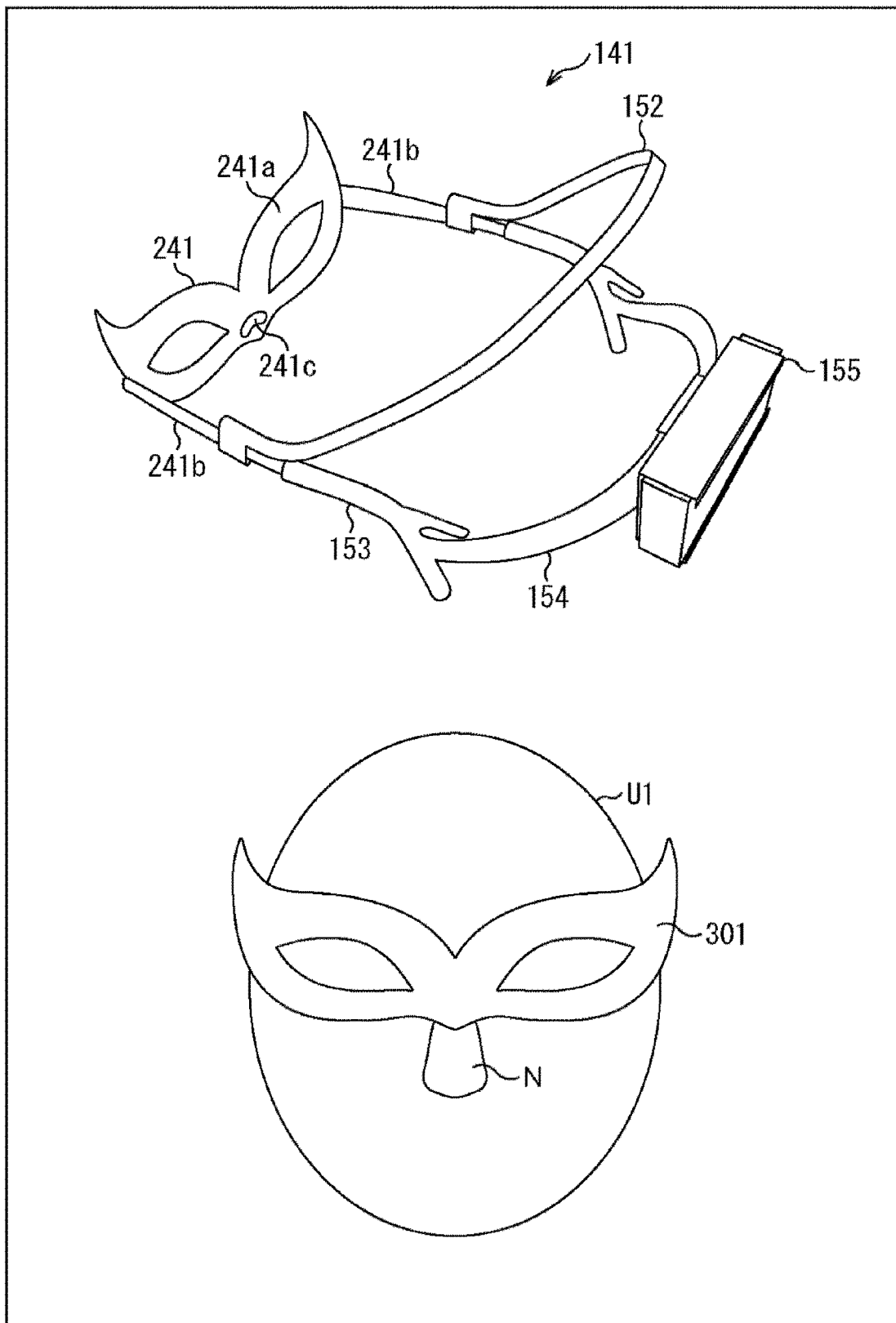
FIG. 25 is a view illustrating an application example of the configuration that comes into contact with the frontal region.

FIG. 25 illustrates a configuration example of a mounting tool 141 in which Venetian glasses 241 are used instead of the glasses 151.

That is, as long as the frontal region corresponding to the frame 151a and the temple 151b of the glasses 151 can be fixed, the configuration may be other than the glasses 151, and may be a configuration such as Venetian glasses 241, for example.

The Venetian glasses 241 comprise a frame 241a, temples 241b, and a nose pad 241c, which respectively correspond to the frame 151a, the temples 151b, and the nose pad 151c in the glasses 151.

As a result, it becomes possible to suppress occurrence of displacement of the mounting tool 141 accompanied by movement of the head of the user U1 due to the weight of the sensor device 10F and to mount the sensor device 10F on the head of the user U1 in a stable state. In addition to the glasses 151 and the Venetian glasses 241, note that a mask having a similar structure or the like may be employed.

9. First Application Example

The above description has explained an example in which the user himself directly grasps the temples 151b and the insertion portions 152a and 153a and adjusts the insertion depth of the temples 151b to adjust the contact pressure to the frontal region and the contact pressure to the occipital region by the occipital region fixing unit 154. However, the insertion depth may be realized by dial adjustment or the like.

Figure 26:
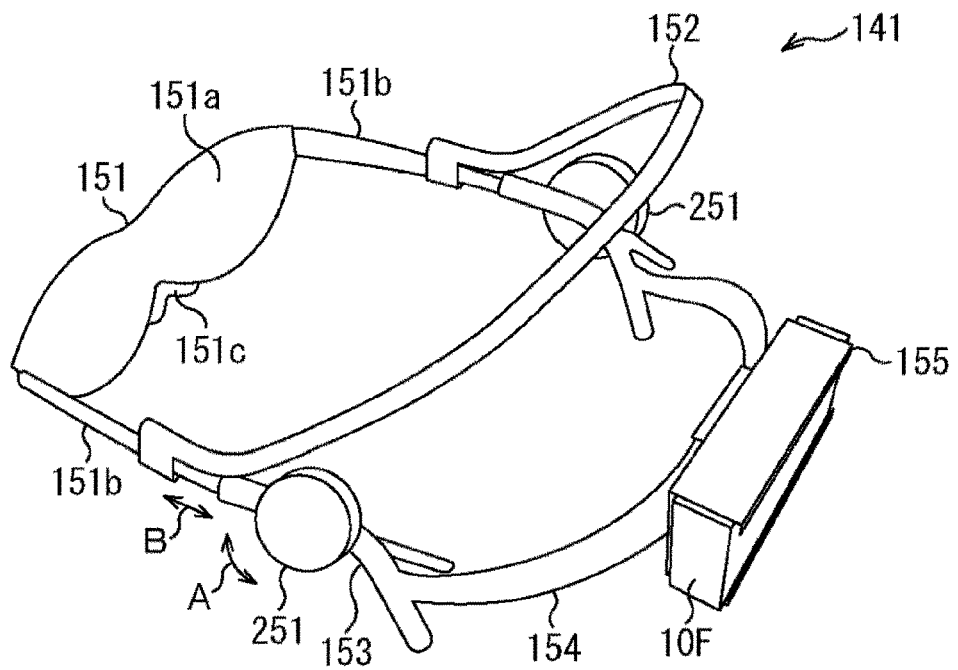
FIG. 26 is a view illustrating a first application example of a mounting tool.

That is, for example, the insertion depth of the temples 151b indicated by the direction of arrow B can be adjusted by providing dials 251 in the vicinity of the insertion portions 153a as illustrated in FIG. 26 and rotating the dials in the direction of arrow A in the figure.

In this case, the insertion depth of the temples 151b with respect to the insertion portions 152a and 153a may be adjusted by a rack and opinion mechanism with respect to rotation of the dials 251.

Furthermore, the insertion portions 152a and 153a may be integrated, the dials 251 may be fixed to the integrated insertion portions 152a and 153a, and moreover, the temples 151b may be each configured as a wire shape to correspond to the rotation of rotating shafts of the dials 251 so as to wind up or open the wire-shaped temples 151b, so that the insertion depth of the temples 151b with respect to the insertion portions 152a and 153a can be adjusted.

It becomes easy with such a configuration to adjust the insertion depth of the temples 151b. Furthermore, in such a configuration, it also becomes possible to suppress occurrence of displacement of the mounting tool 141 accompanied by movement of the head of the user U1 due to the weight of the sensor device 10F, and to mount the sensor device 10F on the head of the user U1 in a stable state.

10. Second Application Example

The above description has explained an example in which the user himself directly grasps the temples 151b and the insertion portions 152a and 153a to adjust the insertion depth of the temples 151b or adjusts the insertion depth by rotating the dials 251, so as to adjust the contact pressure to the frontal region and the contact pressure to the occipital region by the occipital region fixing unit 154.

However, as long as the contact pressure to the frontal region and the contact pressure to the occipital region by the occipital region fixing unit 154 can be adjusted, a method other than adjusting the insertion depth may be employed for adjustment.

Figure 27:
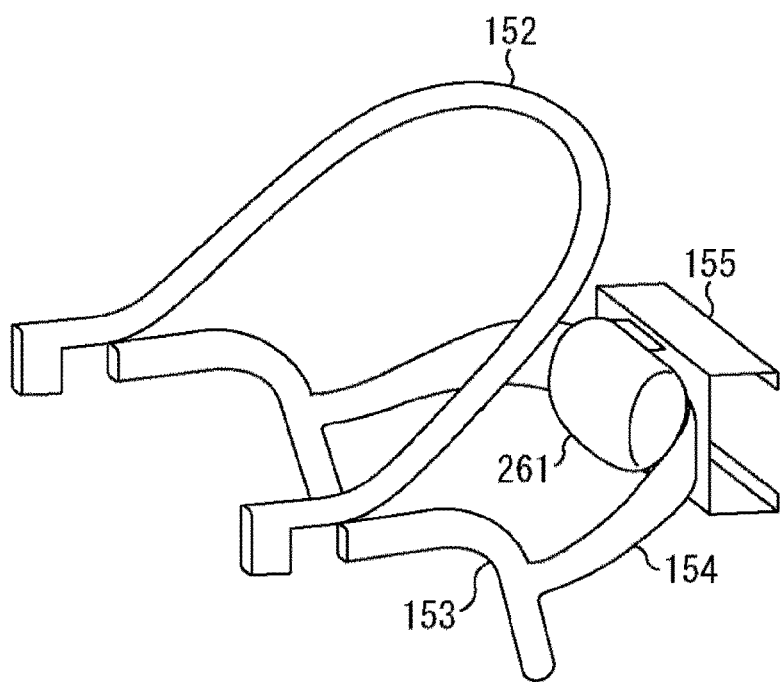
FIG. 27 is a view illustrating a second application example of a mounting tool.

FIG. 27 illustrates a configuration example of a mounting tool 141 having an airbag 261, which is provided on the back side of an occipital region fixing unit 154 where a bracket 155 is mounted and at a site that comes into contact with the occipital region.

The airbag 261 has a bag-shaped structure having a size that changes according to the amount of air injected, and moreover, an air injection/exhaust unit (not shown) is connected, so that the size can be changed depending on the amount of internal air according to injection or exhaust of air.

Accordingly, the user U1 operates the air injection/exhaust unit to change the size of the airbag 261 so as to adjust the contact pressure to the frontal region by the glasses 151 and the contact pressure to the occipital region by the occipital region fixing unit 154. Note that the injection/exhaust unit may be, for example, a push-type inflator.

11. Third Application Example

Although the above description has explained an example of fixing the occipital region upper portion and the occipital region by the contact pressure to the occipital region upper portion by the occipital region upper portion fixing unit 152 and the contact pressure to the occipital region by the occipital region fixing unit 154, a strap connecting the occipital region upper portion fixing unit 152 and the occipital region fixing unit 154 may be further provided so as to appropriately maintain the distance between the occipital region upper portion fixing unit 152 and the occipital region fixing unit 154.

Figure 28:
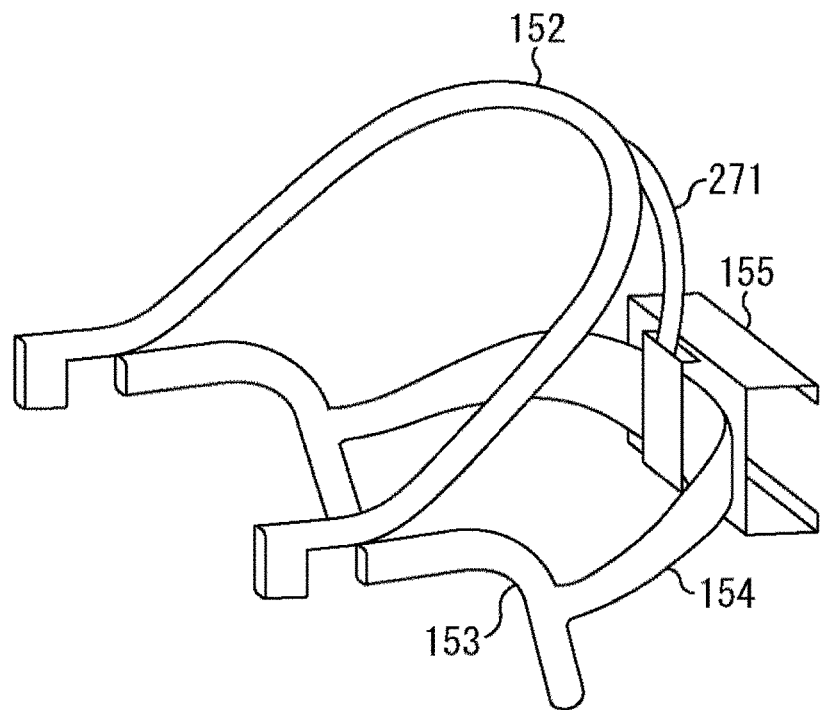
FIG. 28 is a view illustrating a third application example of a mounting tool.

FIG. 28 illustrates a configuration example of a mounting tool 141 in which a strap 271 that connects the occipital region upper portion fixing unit 152 and the occipital region fixing unit 154 is provided.

The strap 271 has a non-stretchable configuration and fixes the distance between the occipital region upper portion fixing unit 152 and the occipital region fixing unit 154.

With such a strap 271, since the distance between the occipital region upper portion fixing unit 152 and the occipital region fixing unit 154 is maintained in an appropriate state, the contact pressure to the occipital region upper portion and the occipital region can be maintained in an appropriate state. Therefore, even when the sensor device 10F is mounted, it is possible to prevent displacement of the mounting tool 141 accompanied by movement of the head of the user U1 due to the weight of the sensor device 10F.

12. Fourth Application Example

Whether the mounting tool 141 is mounted on the head of the user U1 at an appropriate angle or not may be checked.

Figure 29:
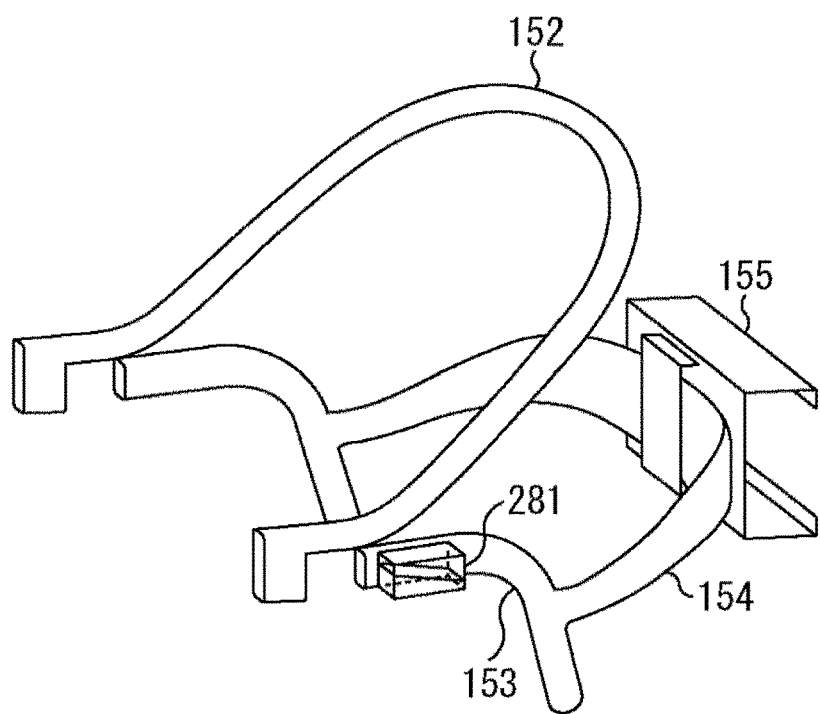
FIG. 29 is a view illustrating a fourth application example of a mounting tool.

FIG. 29 illustrates a configuration example of a mounting tool 141 provided with a spirit level 281.

That is, the mounting tool 141 of FIG. 29 has the spirit level 281 provided on an ear hook 153, and the angle of the mounting tool 141 in a state being mounted on the head of the user U1 can be visually recognized.

The user U1 can check whether the mounting tool 141 is appropriately mounted or not and make adjustment by checking the angle indicated on the spirit level 281 with a mirror or the like while the mounting tool 141 is mounted, for example.

It becomes possible with such a configuration to improve the accuracy of the sensing result by the sensor device 10F provided on the head.

13. Fifth Application Example

Although the above description has explained a configuration example in which the spirit level 281 is provided so that whether the mounting tool 141 is mounted at an appropriate angle with respect to the head of the user U1 or not is checked, whether the mounting is appropriately performed or not may be determined by a different method.

Figure 30:
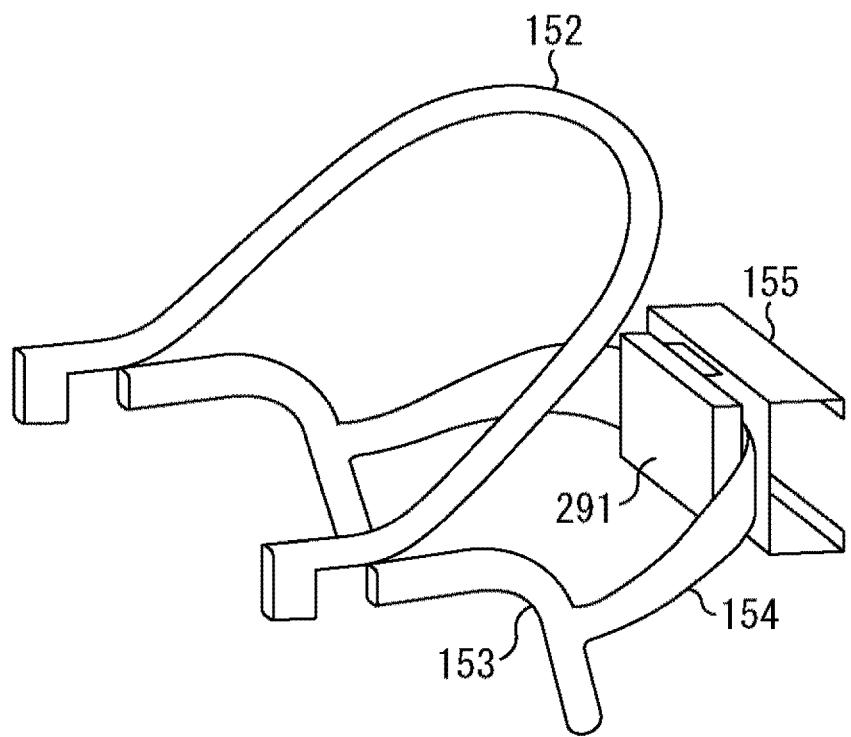
FIG. 30 is a view illustrating a fifth application example of a mounting tool.

FIG. 30 illustrates a configuration example of a mounting tool 141 in which a pressure sensor 291 is provided at a site of the bracket 155 to come into contact with the occipital region on a back side where the sensor device 10F is mounted.

The pressure sensor 291 measures the contact pressure in coming into contact with the occipital region when the mounting tool 141 is mounted with the sensor device 10F mounted on the bracket 155 as pressure distribution at a plurality of points or a surface.

Furthermore, the pressure sensor 291 stores the pressure distribution at points or a surface of the contact pressure to come into contact with the occipital region in a state where the mounting tool 141 is appropriately mounted.

Then, the pressure sensor 291 compares the pressure distribution that is the measurement result with stored pressure distribution, then calculates the difference between points or the sum of differences between points over the entire surface, and judges that the mounting tool 141 is not appropriately mounted and gives a report to the user in a case where the difference or the sum of differences is larger than a predetermined value.

As a reporting method, for example, a buzzer sound may be generated from a speaker (not shown), or a marker lamp (not shown) may be turned on.

With such a configuration, it is possible to cause the user U1 to recognize that the mounting tool 141 is not appropriately mounted, and the user U1 can repeatedly adjust the wearing state until the mounting tool 141 can be appropriately mounted.

As a result, it becomes possible to improve the accuracy of the sensing result by the sensor device 10F provided on the head.

Note that the present disclosure may also have the following configurations.

<1> A mounting tool including:
 a frontal region fixing unit that comes into contact with and fixes the frontal region of the user;
 an occipital region fixing unit that comes into contact with and fixes the occipital region of the user; and
 a sensor device fixing unit configured to fix a sensor device that is provided on a rear surface of the occipital region fixing unit with respect to a surface to come into contact with the occipital region of the user and detects the position and the orientation of the head of the user.

<2> The mounting tool according to <1>,
 in which the frontal region fixing unit has a rod-shaped site extending toward the temporal region,
 an ear hook that is configured integrally with the occipital region and is hung on an ear of the user is further provided, and
 the ear hook has an ear hook insertion portion that allows a rod-shaped site to be inserted and fixes the rod-shaped site in a state of being inserted at a predetermined insertion depth.

<3> The mounting tool according to <2>,
 in which the ear hook insertion portion has a size that allows the rod-shaped site to be inserted, has stretchability, and further has flexibility to fix the rod-shaped site in a state of being inserted at a predetermined insertion depth.

<4> The mounting tool according to <3>,
 in which the ear hook insertion portion includes thermoplastic elastomer, silicone rubber, or natural rubber.

<5> The mounting tool according to <3>,
 in which the opening through which the rod-shaped site of the ear hook insertion portion is inserted has:
 a first elliptical portion having an elliptical shape at a predetermined insertion depth, the first elliptical portion including a major axis, which is in a predetermined direction orthogonal to a predetermined insertion depth direction, larger than a diameter of the rod-shaped site and a minor axis smaller than the diameter of the rod-shaped site; and
 a second elliptical portion having an elliptical shape at an insertion depth different from the predetermined insertion depth, the second elliptical portion including a major axis in a direction deviated by 90 degrees from the predetermined direction orthogonal to the predetermined insertion depth direction and a minor axis smaller than the diameter of the rod-shaped site.

<6> The mounting tool according to <3>,
 in which the ear hook insertion portion further includes a lock mechanism that locks an insertion depth in a state where the rod-shaped site is inserted at a predetermined insertion depth.

<7> The mounting tool according to any one of <1> to <6>, further including
 an occipital region upper portion fixing unit that comes into contact with and fixes an occipital region upper portion, which is an upper portion of the occipital region of the user.

<8> The mounting tool according to <7>,
 in which the frontal region fixing unit has a rod-shaped site extending toward the temporal region, and
 the occipital region upper portion fixing unit has an occipital region upper portion fixing unit insertion portion that allows the rod-shaped site to be inserted at an end portion and fixes the rod-shaped site in a state of being inserted at a predetermined insertion depth.

<9> The mounting tool according to <8>,
in which the occipital region upper portion fixing unit insertion portion has flexibility to allow the rod-shaped site to be inserted and stretchability that fixes the rod-shaped site in a state of being inserted at a predetermined insertion depth.

<10> The mounting tool according to <8>,
in which the occipital region upper portion fixing unit insertion portion includes thermoplastic elastomer, silicone rubber, or natural rubber.

<11> The mounting tool according to <7>, further including
an ear hook that is configured integrally with the occipital region fixing unit and is hung on an ear of the user,
in which the occipital region upper portion fixing unit comes into contact with an area from between the frontal region fixing unit and the ear hook to the occipital region upper portion in a band shape.

<12> The mounting tool according to <7>, further including
an ear hook that is configured integrally with the occipital region fixing unit and is hung on an ear of the user,
in which the occipital region upper portion fixing unit comes into contact with an area from between the occipital region fixing unit and the ear hook up to the occipital region upper portion in a band shape.

<13> The mounting tool according to <7>, further including
a strap connecting substantially central positions of the occipital region fixing unit and the occipital region upper portion fixing unit.

<14> The mounting tool according to <2>,
in which the frontal region fixing unit is a pair of glasses, and
the rod-shaped site is a temple of the glasses.

<15> The mounting tool according to <1>,
in which the frontal region fixing unit is a forehead contact portion that comes into contact with the forehead of the user.

<16> The mounting tool according to <15>,
in which the forehead contact portion comes into contact with the entire surface of the forehead of the user.

<17> The mounting tool according to <15>,
in which the forehead contact portion includes a left portion on the left side and a right portion on the right side substantially of the center, and
respective tips of the left portion and the right portion are provided with detachable portions that can be detached from each other.

<18> The mounting tool according to <15>,
in which the forehead contact portion includes:
a left forehead contact portion that comes into contact with a left surface of the forehead of the user; and
a right forehead contact portion that comes into contact with a right surface of the forehead of the user, and
the left forehead contact portion and the right forehead contact portion are independently configured as separate bodies.

<19> The mounting tool according to any one of <1> to <18>,
in which the occipital region fixing unit further includes an airbag, which has a size that changes according to the amount of air and changes the pressure to come into contact with the occipital region, on a surface to come into contact with the occipital region.

<20> The mounting tool according to any one of <1> to <18>,
in which the occipital region fixing unit further includes a pressure detection unit that detects a pressure distribution of contact with the occipital region, and
the pressure detection unit reports a comparison result on the basis of comparison between measured pressure distribution and pressure distribution of a case where the mounting tool is appropriately mounted.

<21> The mounting tool according to <15>,
in which the frontal region fixing unit and the occipital region fixing unit are integrated.

REFERENCE SIGNS LIST 10, 10A to 10F Sensor device
12 Gyro sensor
14 Acceleration sensor
16 Control unit
18 Communication unit
20 Hub device
30 Information processing device
141 Mounting tool
151 Glasses
151a Frame
151b Temple (bow)
151c Nose pad
152, 152' Occipital region upper portion fixing unit
152a Insertion portion
153 Ear hook
153a, 153a' Insertion portion
154 Occipital region fixing unit
155 Bracket
171, 172 Elliptical portion
181 Lock mechanism
181a Lever
181b Shaft
181c Claw
181d Holder
201 Frontal region fixing band
201a Band portion
201b Insertion rod portion
211 Frontal region fixing band
211L Left band portion
211R Right band portion
212 Detachable portion
212L Left detachable portion
212R Right detachable portion
221 Frontal region fixing unit
221L Left frontal region fixing unit
221R Right frontal region fixing unit
241 Venetian glass
251 Dial
261 Airbag
271 Strap
281 Spirit level
291 Pressure sensor

The invention claimed is:
1. A motion capture system comprising:
a head sensor mounting device including:
an occipital region fixing unit configured to come into contact with and fix an occipital region of a user; and
a head sensor device fixing unit that is provided on a back side of the occipital region fixing unit configured to come into contact with the occipital region of the user, wherein the head sensor device fixing unit is configured to fix, with a head sensor bracket, a sensor device for a head of the user that retrieves head sensor data including a position and an orientation of the head of the user;

a waist sensor mounting device including:
   a waist sensor device fixing unit configured to fix, with a waist sensor bracket, a sensor device for a waist of the user that retrieves waist sensor data including a position and an orientation of the waist of the user, the sensor device for the waist being provided as a clip configured to hang on the waist of the user;

a wrist sensor mounting device including:
   a wrist belt configured to wind around a wrist of the user; and
   a wrist sensor device fixing unit configured to fix, with a wrist sensor bracket, a sensor device for the wrist of the user that retrieves wrist sensor data including a position and an orientation of the wrist of the user; and an ankle sensor mounting device including:
   an ankle belt configured to wind around an ankle of the user; and
   an ankle sensor device fixing unit configured to fix, with an ankle sensor bracket, a sensor device for the ankle of the user that retrieves ankle sensor data including a position and an orientation of the ankle of the user, wherein the sensor device for the head of the user, the sensor device for the waist of the user, the sensor device for the wrist of the user, and the sensor device for the ankle of the user are mounted on the head sensor device fixing unit, the waist sensor device fixing unit, the wrist sensor device fixing unit and the ankle sensor device fixing unit respectively, wherein each of the sensor device for the head of the user, the sensor device for the waist of the user, the sensor device for the wrist of the user, and the sensor device for the ankle of the user includes
   a motion sensor configured to acquire a respective one of the head sensor data, the waist sensor data, the wrist sensor data, or the ankle sensor data, and
   a communication unit configured to wirelessly transmit the respective one of the head sensor data, the waist sensor data, the wrist sensor data, or the ankle sensor data to an information processing apparatus.

2. The motion capture system according to claim 1, wherein
   the information processing apparatus is configured to estimate skeleton data of the user based on the head sensor data, the waist sensor data, the wrist sensor data, and the ankle sensor data transmitted from a respective one of the sensor device for the head of the user, the sensor device for the waist of the user, the sensor device for the wrist of the user, and the sensor device for the ankle of the user mounted on a respective one of the head sensor mounting device, the waist sensor mounting device, the wrist sensor mounting device and the ankle sensor mounting device, the skeleton data including portions of the user at which the sensor device for the head of the user, the sensor device for the waist of the user, the sensor device for the wrist of the user, and the sensor device for the ankle of the user are attached to and portions of the user at which the sensor device for the head of the user, the sensor device for the waist of the user, the sensor device for the wrist of the user, and the sensor device for the ankle of the user are not attached to.

3. The motion capture system according to claim 1, wherein the motion sensor is at least one of a gyro sensor, an acceleration sensor, or a geomagnetic sensor.

4. The motion capture system according to claim 1, wherein skeleton data is estimated by using inverse kinematics calculation based on the head sensor data, the waist sensor data, the wrist sensor data, and the ankle sensor data transmitted from the respective one of the sensor device for the head of the user, the sensor device for the waist of the user, the sensor device for the wrist of the user, and the sensor device for the ankle of the user.

5. The motion capture system according to claim 4, wherein the information processing apparatus is configured to output visualized skeleton data based on the skeleton data.

6. The motion capture system according to claim 4, wherein the information processing apparatus is configured to output a 3D model reflecting the skeleton data.

7. The motion capture system according to claim 1, wherein the wrist sensor device fixing unit and the ankle sensor device fixing unit are respectively configured to fix the sensor device for the wrist of the user and the sensor device for the ankle of the user by a claw portion of a respective one of the wrist sensor bracket and the ankle sensor bracket.

8. The motion capture system according to claim 1, wherein the waist sensor device fixing unit is configured to fix the sensor device for the waist of the user by a claw portion of the waist sensor bracket.

9. The motion capture system according to claim 1, wherein the communication unit wirelessly transmits the respective one of the head sensor data, the waist sensor data, the wrist sensor data, or the ankle sensor data to the information processing device using Bluetooth.

10. The motion capture system according to claim 1, wherein the occipital region fixing unit includes a stretchable material.

11. A motion capture system comprising:
a head sensor mounting device including:
   an occipital region fixing unit configured to come into contact with and fix an occipital region of a user;
   a head sensor device fixing unit that is provided on a back side of the occipital region fixing unit configured to come into contact with the occipital region of the user, wherein the head sensor device fixing unit is configured to fix, with a head sensor bracket, a sensor device for a head of the user that retrieves head sensor data including a position and an orientation of the head of the user; and
   the sensor device for the head of the user mounted on the head sensor device fixing unit;

a waist sensor mounting device including:
   a waist sensor device fixing unit configured to fix, with a waist sensor bracket, a sensor device for a waist of the user that retrieves waist sensor data including a position and an orientation of the waist of the user, the sensor device for the waist being provided as a clip configured to hang on the waist of the user; and
   the sensor device for the waist mounted on the waist sensor device fixing unit;

a wrist sensor mounting device including:
   a wrist belt configured to wind around a wrist of the user;

a wrist sensor device fixing unit configured to fix, with a wrist sensor bracket, a sensor device for the wrist of the user that retrieves wrist sensor data including a position and an orientation of the wrist of the user; and the sensor device for the wrist mounted on the wrist sensor device fixing unit; and an ankle sensor mounting device including:
- an ankle belt configured to wind around an ankle of the user;
- an ankle sensor device fixing unit configured to fix, with an ankle sensor bracket, a sensor device for the ankle of the user that retrieves ankle sensor data including a position and an orientation of the ankle of the user; and
- the sensor device for the ankle mounted on the ankle sensor device fixing unit, wherein each of the sensor device for the head of the user, the sensor device for the waist of the user, the sensor device for the wrist of the user, and the sensor device for the ankle of the user includes
- a motion sensor configured to acquire a respective one of the head sensor data, the waist sensor data, the wrist sensor data, or the ankle sensor data, and
- a communication unit configured to wirelessly transmit the respective one of the head sensor data, the waist sensor data, the wrist sensor data, or the ankle sensor data to an information processing apparatus.

* * * * *